US012378203B2

(12) United States Patent
Verma et al.

(10) Patent No.: US 12,378,203 B2
(45) Date of Patent: Aug. 5, 2025

(54) IMIDAZOLE COMPOUNDS, PROCESS FOR THE SYNTHESIS AND USES THEREOF

(71) Applicant: AHAMMUNE BIOSCIENCES PRIVATE LIMITED, Pune (IN)

(72) Inventors: Mahesh Kumar Verma, Pune (IN); Kashinath Komirishetty, Pune (IN); Parul Ganju, Pune (IN); Sudhanand Prasad, Pune (IN); Annie Richharia, Pune (IN); Sanket Sanjay Shete, Pune (IN)

(73) Assignee: AHAMMUNE BIOSCIENCES PRIVATE LIMITED, Pune (IN)

( * ) Notice: Subject to any disclaimer, the term of this patent is extended or adjusted under 35 U.S.C. 154(b) by 1019 days.

(21) Appl. No.: 17/290,277

(22) PCT Filed: Nov. 1, 2019

(86) PCT No.: PCT/IB2019/059389
§ 371 (c)(1),
(2) Date: Apr. 30, 2021

(87) PCT Pub. No.: WO2020/089844
PCT Pub. Date: May 7, 2020

(65) Prior Publication Data
US 2021/0380538 A1 Dec. 9, 2021

(30) Foreign Application Priority Data

Nov. 1, 2018 (IN) .............................. 201821041355

(51) Int. Cl.
| | |
|---|---|
| *C07D 233/54* | (2006.01) |
| *C07D 401/04* | (2006.01) |
| *C07D 401/06* | (2006.01) |
| *C07D 403/10* | (2006.01) |
| *C07D 405/04* | (2006.01) |
| *C07D 417/14* | (2006.01) |
| *C07D 471/14* | (2006.01) |

(52) U.S. Cl.
CPC ......... *C07D 233/54* (2013.01); *C07D 401/04* (2013.01); *C07D 401/06* (2013.01); *C07D 403/10* (2013.01); *C07D 405/04* (2013.01); *C07D 417/14* (2013.01)

(58) Field of Classification Search
CPC .. C07D 233/54; C07D 233/64; C07D 401/04; C07D 401/06; C07D 417/14; C07D 403/10; C07D 405/04; A61P 17/00; A61P 37/00
See application file for complete search history.

(56) References Cited

U.S. PATENT DOCUMENTS

| | | | |
|---|---|---|---|
| 5,712,392 | A | 1/1998 | Thurkauf et al. |
| 2003/0018025 | A1 | 1/2003 | Thurkauf et al. |
| 2016/0046598 | A1 | 2/2016 | Nebolsin et al. |
| 2017/0183318 | A1 | 6/2017 | Nebolsin et al. |

FOREIGN PATENT DOCUMENTS

| | | | |
|---|---|---|---|
| EP | 2 985 282 A1 | 2/2016 | |
| GB | 1 341 375 A | 12/1973 | |
| JP | 2001026582 A | 1/2001 | |
| JP | 4230156 B2 | 12/2008 | |
| JP | 2016-516766 | 6/2016 | |
| JP | 2017-511374 | 4/2017 | |
| WO | WO-02083111 A2 * | 10/2002 | ............. A61K 31/00 |
| WO | WO 2002083111 A2 | 10/2002 | |
| WO | WO 03/094839 A2 | 11/2003 | |
| WO | WO 2007/067752 A2 | 6/2007 | |
| WO | WO 2011/002067 A1 | 1/2011 | |

(Continued)

OTHER PUBLICATIONS

Gleave R J et al: "Synthesis and biological activity of a series of tetrasubstituted-imidazoles as P2X 7 antagonists" Bioorganic & Medicinal Chemistry Letters, Elsevier, Amsterdam, NL, vol. 20, No. 16, Aug. 15, 2010 (Aug. 15, 2010), pp. 4951-4954, XP027172657, ISSN: 0960-894X [retrieved on Jun. 25, 2010].

European Extended Search Report mailed on Aug. 8, 2022, in European Application No. 19878005.8.

Andrew Thurkauf et al., 2-Phenyl-4-(aminomethyl)imidazoles as Potential Antipsychotic Agents. Synthesis and Dopamine D2 Receptor Binding; Journal of Medicinal Chemistry 1995 38 (12), 2251-2255.

International Search Report mailed on Feb. 6, 2020, in the PCT Application No. PCT/IB2019/059389.

(Continued)

*Primary Examiner* — Adam C Milligan
*Assistant Examiner* — Sophia P Hirakis
(74) *Attorney, Agent, or Firm* — Trupti P. Joshi

(57) ABSTRACT

The present invention relates to novel pharmaceutical agents and the process of preparation thereof. The present invention discloses compounds of general formula I, and the process of their preparation. The compounds of the invention are useful in the treatment and prevention of diseases related to cellular stress mediated immune deregulation and loss of homeostasis also including autoimmune diseases, cancers, metabolic, dermatological, cardiovascular and neurodegenerative diseases.

Formula - I

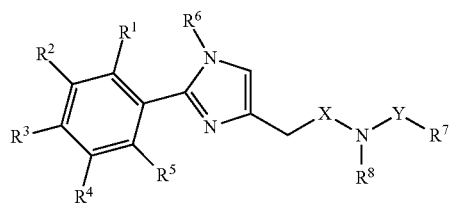

13 Claims, No Drawings

(56) References Cited

FOREIGN PATENT DOCUMENTS

WO  WO 2016/087352 A1  6/2016

OTHER PUBLICATIONS

Written Opinion mailed on Feb. 6, 2020, in the PCT Application No. PCT/IB2019/059389.
Madsen, Christian et al.: "5-Substituted Imidazole-4-Acetic Acid Analogues: Synthesis, Modeling, and Pharmacological Characterization of a Series of Novel-Aminobutyric Acidc Receptor Agonists", Journal of Medicinal Chemistry, vol. 50, No. 17, 2007, pp. 4147-4161, XP002676857, Doi: 10.1021/JM070447J *.
Huang, Y. et al.: "Synthesis of 2-(2, 3-dimethoxyphenyl)-4-(aminomethyl) imidazole Analogues and their Binding Affinities for Dopamine D2 and D3 Receptors", Bioorganic & Medicinal Chemistry, vol. 9, No. 12, 2001, pp. 3113-3122, XP002674312, DOI: 10.1016/S0968-0896(01)00175-4 *.
Abdellattif, M. H. et al.: "Henry Reaction between Benzaldehyde and Nitromethane over Solid Base Catalysts: A Green Protocol", Green and Sustainable Chemistry, vol. 8, No. 2, 2018, pp. 139-155, XP055702716 *.
Bachman, G. B. et al.: "Nitration studies. XVIII. Conversion of lower nitroalkanes to higher members of the series", The Journal of Organic Chemistry, vol. 37, No. 18, 1972, pp. 2810-2814, XP055702776 *.
Ramadas, K. et al.: "Iron-ammonium chloride-a convenient and inexpensive reductant", Synthetic Communications, vol. 22, No. 22, 1992, pp. 3189-3195, XP055490295, DOI: 10.1080/00397919208021132 *.
Ouellette, R.J. et al.: "Principles of Organic Chemistry", Elsevier Science, 2015, pp. 341,381, Retrieved from the Internet <URL:https://books.google.co.in/books?id=U-CoBAAAQBAJ> *.
Registry(STN) [online], Entered STN: Jun. 29, 2015, [retrieved on Sep. 7, 2023], CAS registration No. 1791178-01-2.
Registry(STN) [online], Entered STN: Jun. 28, 2015, [retrieved on Sep. 7, 2023], CAS registration No. 1790267-15-0.
Registry(STN)[online], before Nov. 1, 2018, [search date Sep. 7, 2023], 4th and 8th compounds from the top, etc.

* cited by examiner

IMIDAZOLE COMPOUNDS, PROCESS FOR THE SYNTHESIS AND USES THEREOF

CROSS-REFERENCE TO RELATED APPLICATIONS

The present application is a § 371 national stage application of International Application No. PCT/IB2019/059389, filed Nov. 1, 2019, which claims the benefit of priority from Indian Application No. 201821041355, filed Nov. 1, 2018.

FIELD OF THE INVENTION

The present invention relates to novel pharmaceutical agents and the process of preparation thereof. The present invention discloses compounds that are useful in the treatment and prevention of diseases related to cellular stress mediated immune deregulation and loss of homeostasis. These include autoimmune diseases, cancers, metabolic, dermatological, cardiovascular and neurodegenerative diseases.

BACKGROUND OF THE INVENTION

The immune system is a collection of special cells and chemicals that fight infection-causing agents such as bacteria and viruses. An autoimmune disorder occurs when a person's immune system mistakenly attacks their own body cells and tissues. Autoimmune disorders are broadly grouped into two categories—'organ-specific' meaning only one organ is affected, while in 'systemic' disorders, multiple organs or body systems may be affected.

There are a large number of different autoimmune disorders ranging in severity from mild to disabling, depending on which system of the body is under attack and to what degree. It has also been observed that, women are more susceptible than men, particularly during their childbearing years. It is thought that sex hormones may be at least partly responsible.

Autoimmune diseases are characterized by an abnormal immune response involving either cells or antibodies, that are in either case directed against normal autologous tissues. Both adaptive immune responses, comprising T-cell mediated immunity and humoral immune response, involving antibody-mediated immunity is involved in the trigger and spread of autoimmune diseases.

The triggers of autoimmunity are not well understood. Till recent years, studies on etiopathogenesis of autoimmune diseases have focused on the role of immune components. However, several studies have now highlighted the synergistic role of target tissues in spread of autoimmunity. A common pathway that has emerged in these studies is endoplasmic reticulum stress (ER stress). ER is a major cellular organelle that is associated with critical functions involving cellular homeostasis including protein synthesis, folding and quality control, antigen processing and presentation, calcium control and redox balance. The physiological activity of the ER is tightly controlled by cell intrinsic as well as extrinsic processes. Disturbance in the functioning of ER triggers a stress response called ER stress that activates intracellular signaling pathways, constituting the unfolded protein response (UPR) targeted to manage stress conditions. However, inability to manage ER stress is implicated in a number of pathological conditions including cancers, metabolic, dermatological, cardiovascular and neurodegenerative diseases. In addition, aberrant regulation of ER stress is associated with early autoimmune events. For instance, misfolding of proteins and alteration in antigen processing can lead to immunogenic neoantigen formation. Further, stressed cells could be inadequate to support tolerance mechanisms in autoreactive cells, which are less susceptible to programmed cell death, perpetuating autoimmunity in diseases like type I diabetes, rheumatoid arthritis, psoriatic arthritis, multiple sclerosis, lupus, celiac disease, pernicious anaemia. ER stress mechanisms attain special interest in the physiology of skin, an organ that is constantly exposed to the external environment. In fact, deregulation of ER stress mechanisms is associated with several skin autoimmune diseases, including Vitiligo, psoriasis, SLE, pemphigus, scleroderma etc. Targeting ER stress mechanisms thus represents a potential therapeutic target for autoimmune diseases.

It has been observed that most of the existing therapies for autoimmune disorders aim to provide only symptomatic benefit to patients as there is little by way of targeted and effective therapy. Administration of steroids is one of the most common approach for treatment. However, the non-specific nature and side-effects associated with long-term steroid usage limits their usefulness. As an example, Vitiligo is an autoimmune disease where dysregulation of immune functions takes place with increased levels of inflammatory cytokines in the lesion. Hence, topical corticosteroids become the most common first line therapy. Patients are also advised to expose themselves to sunlight in order to increase melanin synthesis. Phototherapy (narrowband UVB or 311 nm laser) is generally included with topical steroids to achieve better results. However, a number of patients don't achieve the desired level of pigmentation which adds to their psychological burden. At times, dermatologists are unable to tell the possible success of the therapy being administered, hence patients remain uncertain about the duration and outcome of the treatment. Clearly, new therapies targeting relevant pathways involved in triggering autoimmune responses are need of the hour.

The embodiments of the present invention provide for chemical entities that modulate cellular stress. More specifically, the chemical entities rescue cells from stress mediated death and thus impede cascade of events leading to aberrant regulation of immunity. These chemical entities thus offer potential for prevention and treatment of immune-related disorders and diseases.

SUMMARY OF THE INVENTION

The present invention relates to a novel pharmaceutical compound having the general formula I as defined:

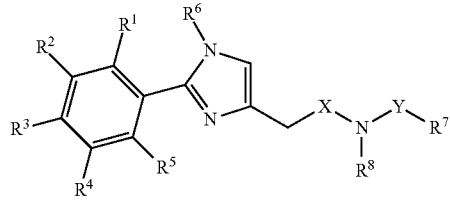

Formula - I

Wherein,
$R^1$, $R^2$, $R^3$, $R^4$, $R^5$ are each independently selected from a hydrogen, halogen, straight chain or branched alkyl, straight chain or branched alkenyl, straight chain or branched alkoxyalkyl, phenyl, aryl, aralkyl, alkoxy alkyl, alkoxy aryl, aromatic or aliphatic heterocycle comprising at least one hetero atom selected from a group of O, N and S;

any of two adjacent R groups form a 5-6 membered aromatic or aliphatic ring comprising at least one hetero atom selected from a group of O, N and S;

$R^6$ independently selected from hydrogen, straight chain or branched Cl-05 alkyl;

X is selected from $CH_2$ or C=O, When X is $CH_2$ Y is C=O and When X is C=O Y is absent;

$R^7$ and $R^8$ are each independently selected from hydrogen, straight chain or branched alkyl, straight chain or branched aralkyl, straight chain or branched alkenyl, straight chain or branched alkynyl; together form a 3-7 membered aromatic or aliphatic heterocycle comprising at least one hetero atom selected from O, N, and S, $-CH_2(CH_2)_nNR_cR_d$ wherein n is 0-3, and $R_c$, and $R_d$ are both independently selected from alkyl or together form a 3-7 membered aromatic or aliphatic heterocycle comprising at least one hetero atom selected from a group of O, N and S; and their stereoisomers (diastereoisomers, enantiomers), pure or mixed, racemic mixtures, geometrical isomers, tautomers, pharmaceutically acceptable salts, hydrates, solvates, solid forms and mixtures thereof.

All the substituents $R^1$, $R^2$, $R^3$, $R^4$, $R^5$, $R^6$, $R^7$, $R^8$ of the general formula I may also be further substituted or remain unsubstituted.

The present invention also relates to the process of preparation of the compound having general formula I:

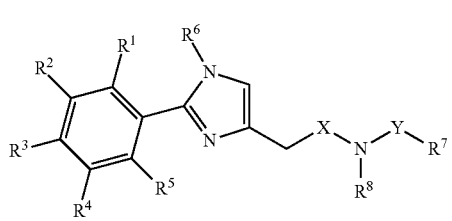

Formula - I

Wherein, $R^1$, $R^2$, $R^3$, $R^4$, $R^5$ are each independently selected from a hydrogen, halogen, straight chain or branched alkyl, straight chain or branched alkenyl, straight chain or branched alkoxyalkyl, phenyl, aryl, aralkyl, alkoxy alkyl, alkoxy aryl, aromatic or aliphatic heterocycle comprising at least one hetero atom selected from a group of O, N and S;

any of two adjacent R groups form a 5-6 membered aromatic or aliphatic ring comprising at least one hetero atom selected from a group of O, N and S;

$R^6$ independently selected from Hydrogen, straight chain or branched alkyl;

X is selected from $CH_2$ or C=O, When X is $CH_2$ Y is C=O and When X is C=O Y is absent;

$R^7$ and $R^8$ are each independently selected from hydrogen, straight chain or branched alkyl, straight chain or branched aralkyl, straight chain or branched alkenyl, straight chain or branched alkynyl; together form a 3-7 membered aromatic or aliphatic heterocycle comprising at least one hetero atom selected from O, N, and S, $-CH_2(CH_2)_nNR_cR_d$ wherein n is 0-3, and $R_c$, and $R_d$ are both independently selected from alkyl or together form a 3-7 membered aromatic or aliphatic heterocycle comprising at least one hetero atom selected from a group of O, N and S; and their stereoisomers (diastereoisomers, enantiomers), pure or mixed, racemic mixtures, geometrical isomers, tautomers, pharmaceutically acceptable salts, hydrates, solvates, solid forms and mixtures thereof.

DETAILED DESCRIPTION

The compound of the present invention having the general formula I:

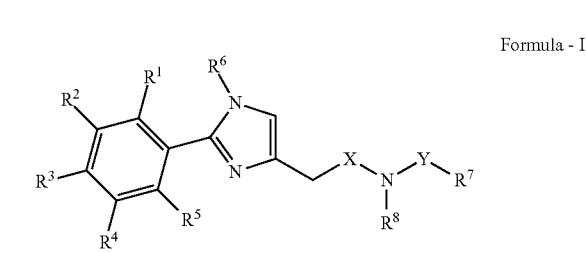

Formula - I

Wherein, $R^1$, $R^2$, $R^3$, $R^4$, $R^5$ are each independently selected from a hydrogen, halogen, straight chain or branched alkyl, straight chain or branched alkenyl, straight chain or branched alkoxyalkyl, phenyl, aryl, aralkyl, alkoxy alkyl, alkoxy aryl, aromatic or aliphatic heterocycle comprising at least one hetero atom selected from a group of O, N and S;

any of two adjacent R groups form a 5-6 membered aromatic or aliphatic ring comprising at least one hetero atom selected from a group of O, N and S;

$R^6$ independently selected from Hydrogen, straight chain or branched alkyl;

X is selected from CH2 or C=O, When X is CH2 Y is C=O and When X is C=O Y is absent;

$R^7$ and $R^8$ are each independently selected from hydrogen, straight chain or branched alkyl, straight chain or branched aralkyl, straight chain or branched alkenyl, straight chain or branched alkynyl;

together form a 3-7 membered aromatic or aliphatic heterocycle comprising at least one hetero atom selected from O, N, and S, $-CH_2(CH_2)_nNR_cR_d$ wherein n is 0-3, and $R_c$, and $R_d$ are both independently selected from alkyl or together form a 3-7 membered aromatic or aliphatic heterocycle comprising at least one hetero atom selected from a group of O, N and S; and their stereoisomers (diastereoisomers, enantiomers), pure or mixed, racemic mixtures, geometrical isomers, tautomers, pharmaceutically acceptable salts, hydrates, solvates, solid forms and mixtures thereof.

All the substituents $R^1$, $R^2$, $R^3$, $R^4$, $R^5$, $R^6$, $R^7$, $R^8$ may also be further substituted or remain unsubstituted.

The present invention discloses compound of general formula I, wherein X is selected from among C=O or $CH_2$. Particularly, when X is $CH_2$, Y is C=O. Further, when X is a carbonyl group, i.e C=O; there is no Y substitution on N, i.e. Y is wholly absent. The present invention discloses compounds of general formula I, wherein $R^1$, $R^2$, $R^3$, $R^4$, $R^5$ is preferably a halogen selected from the Cl, Br, I, and F. The present invention discloses compounds of general formula I, wherein $R^6$ may preferably be hydrogen. The present invention discloses compounds of general formula I, wherein $R^6$ may preferably be methyl.

The pharmaceutically acceptable salts of the compounds of the present invention is selected from a group consisting of hydrochloric acid, hydrobromic acid, nitric acid, sulfuric acid, phosphoric acid, benzenesulfonic acid, methanesulfonic acid, ethanesulfonic acid, toluenesulfornic acid, formamidinesulfonic acid, naphthalenedisulfonic acid, formic acid, fumaric acid, acetic acid, propionic acid, lactic acid, malic acid, citric acids, maleic acid, benzoic acid, malonic acid, tartaric acid, oxalic acid, succinic acid, or salts of sodium, potassium, calcium, magnesium, and ammonium as an active ingredient with one or more pharmaceutically acceptable carriers, diluents or excipients.

In the context of this invention, the term alkyl designates a hydrocarbon radical that is saturated, linear, branched, or cyclic, halogenated or not, having particularly from 1 to 5 carbon atoms, such a methyl, trifluoromethyl, ethyl, n-propyl, isopropyl, n-butyl, isobutyl, tertbutyl, sec-butyl, pentyl.

The term 'alkenyl' refers to a hydrocarbon radical that is unsaturated having one or more carbon-carbon double bond, linear, branched, halogenated, or cyclic having particularly from 2 to 5 carbon atoms.

The term 'alkynyl' refers to a hydrocarbon radical that is unsaturated having one or more carbon-carbon triple bond, linear, branched, halogenated, or cyclic having particularly from 2 to 5 carbon atoms.

The term 'alkoxyalkyl' refers to an alkyl chain linked to an oxygen atom forming an ether bond. The alkyl chain corresponds to the previously expressed definition and includes alkyl groups such as methoxy, trifluoromethoxy, ethoxy, n-propyloxy, isopropyloxy, n-butoxy, isobutoxy, tertbutoxy, sec-butoxy.

The term 'aralkyl' refers to an aryl-substituted alkyl hydrocarbon radical where the hydrocarbon radical comprises about 2-5 carbon atoms.

The term 'cycloalkyl' designates an alkyl group as defined above and forms at least one cycle (e.g. cycloalkyl groups having 3 to 8 carbon atoms: cyclopropyl, cyclobutyl, cyclopentyl, cyclohexyl, cycloheptyl, and cyclooctyl).

The term 'aryl' refers to aromatic groups comprising preferably from 6-10 carbon atoms, possibly interrupted by one or several heteroatoms selected among N, O or S (more specifically call 'heteroaryl'). They are generally mono- or bi-cyclical and comprise preferably from 6 to 14 carbon atoms, such as phenyl, α-naphtyl, β-naphtyl.

The term 'alkoxyaryl' refers to an alkyl group having bonded to an oxygen atom to from an ether bond attached to an aryl group.

The term 'heterocycle' refers to any cycloalkyl group as defined above interrupted by one or more heteroatoms chosen from among O, N and S being aliphatic, aromatic rings being preferably 3-7 membered rings.

The term 'halogen' refers to an atom of fluorine, chlorine, bromine or iodine.

The term 'effective amount', 'pharmaceutically effective amount', or 'therapeutically effective amount' refers to any amount which will cause an improvement or change in the condition or one or more of its symptoms and/or to prevent the occurrence of the disease or disorder and can be determined by standard clinical advancement of the condition, the body surface area affected with the clinical condition, and the type and concentration of formulation administered.

The acronym 'HATU' refers to 1-[Bis(dimethylamino)methylene]-1H-1,2,3-triazolo[4,5-b]pyridinium 3-oxid hexafluorophosphate, Hexafluorophosphate Azabenzotriazole Tetramethyl Uronium; the acronym 'HBTU' refers to 2-(1H-benzotriazol-1-yl)-1,1,3,3-tetramethyluronium hexaflurophosphate, Hexafluorophosphate Benzotriazole Tetramethyl Uronium; the acronym 'EDC' refers to 1-Ethyl-3-(3-dimethylaminopropyl)carbodiimide; the acronym 'DMAP' refers to dimethylaminopyridine; the acronym 'DMF' refers to dimethylformamide; the acronym 'THF' refers to tetrahydrofuran; the acronym 'TFA' refers to Trifluoroacetic acid; the acronym 'DCM' refers to Dichloromethane; the acronym 'DIPEA' refers to N,N-Diisopropylethylamine also known as Hunig's base.

An embodiment of the present invention further discloses the process for preparing the compound of general formula I:

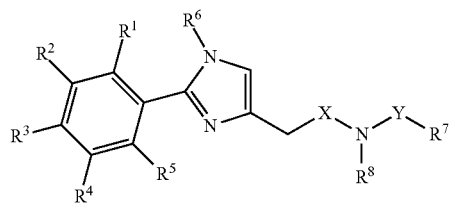

Formula - I

Wherein,
$R^1$, $R^2$, $R^3$, $R^4$, $R^5$ are each independently selected from a hydrogen, halogen, straight chain or branched alkyl, straight chain or branched alkenyl, straight chain or branched alkoxyalkyl, phenyl, aryl, aralkyl, alkoxy alkyl, alkoxy aryl, aromatic or aliphatic heterocycle comprising at least one hetero atom selected from a group of O, N and S;
any of two adjacent R groups form a 5-6 membered aromatic or aliphatic ring comprising at least one hetero atom selected from a group of O, N and S; $R^6$ independently selected from Hydrogen, straight chain or branched alkyl;
X is selected from CH2 or C=O, When X is CH2 Y is C=O and When X is C=O Y is absent;
$R^7$ and $R^8$ are each independently selected from hydrogen, straight chain or branched alkyl, straight chain or branched aralkyl, straight chain or branched alkenyl, straight chain or branched alkynyl; together form a 3-7 membered aromatic or aliphatic heterocycle comprising at least one hetero atom selected from O, N, and S, —CH2(CH2)$_n$NR$_c$R$_d$ wherein n is 0-3, and R$_c$, and R$_d$ are both independently selected from alkyl or together form a 3-7 membered aromatic or aliphatic heterocycle comprising at least one hetero atom selected from a group of O, N and S; and their stereoisomers (diastereoisomers, enantiomers), pure or mixed, racemic mixtures, geometrical isomers, tautomers, pharmaceutically acceptable salts, hydrates, solvates, solid forms and mixtures thereof.

The process for preparation of the compounds of Formula I with steps comprising of:
a. Reacting chlorobenzamidine hydrochloride in the presence of 1,3 dihydroxyacetone dimer resulting in an imidazole compound II;
b. Reacting the imidazole moiety formed in step (a) in the presence of suitable reagent for chlorination to obtain a compound III and then cyanation to obtain a compound IV in the presence of suitable reagent;
c. Reacting the compound IV to undergo hydrolysis resulting in an imidazole moiety comprising carboxylic acid compound V;
d. Reacting the compound V with the desired reagent and undergoes amide coupling to produce the compounds of formula (I); and,
Optionally;
e. Reacting the compound IV formed in step (b) with suitable reagents to form a compound VII;
f. Reacting the compound VII with the desired reagent and undergoes amide coupling to produce the compounds of formula (I).

An embodiment of the present invention is a process of preparing the compounds of Formula I, with steps comprising of:
  a. Reacting chlorobenzamidine hydrochloride or dichlorobenzamidine hydrochloride in the presence of 1,3 dihydroxyacetone dimer resulting in an imidazole compound II or XVI;
  b. Reacting the imidazole compound II or XVI with suitable reagents to obtain a compound X or XVII;
  c. Introducing a nitro group to the imidazole compound X or XVII to obtain a compound XI or XVIII in the presence of suitable reagents;
  d. Hydrogenating the compound XI or XVIII in the presence of suitable reagents to obtain a compound XII or XIX;
  e. Amination of the compound XII or XIX by addition of Fe and $NH_4Cl$ then reacting with di-tert-butyl dicarbonate to obtain a compound XIII or XX;
  f. Treating the compound XIII or XX with desired reagents through amide coupling to obtain the compounds of formula I.

Further, the present invention discloses the compounds of Formula I and their stereoisomers (diastereoisomers, enantiomers), pure or mixed, racemic mixtures, geometrical isomers, tautomers, pharmaceutically acceptable salts, hydrates, solvates, solid forms and mixtures thereof.

Without being bound by theory the inventors of the present invention have contemplated novel and inventive methods for modulating ER stress pathways in cells and/or in vivo.

Accordingly, the present invention discloses compounds of general formula I that have been unexpectedly found to be successful in influencing the ER stress pathways in cells. Going further the inventors envisage that the compounds of general formula I to be useful in the treatment and prevention of diseases associated with deregulation of cellular stress pathways more specifically ER stress. The disease includes but are not limited to diseases triggered by cellular stress including but not limited to autoimmune diseases, cancers, tumors, metabolic disorders, neurodegeneration, cardiovascular, pulmonary, ophthalmic and other dermatological disorders.

The present inventors have found the use of presently disclosed compounds in preventing stress mediated melanocyte death that could find utility in the treatment of dermatological disorders.

It is envisaged that the compounds of the present invention may be utilized separately or in combination with other therapies for the treatment of diseases triggered by cellular stress including but not limited to autoimmune diseases, cancers, tumors, metabolic disorders, neurodegeneration, cardiovascular, pulmonary, ophthalmic and other dermatological disorders.

Another embodiment of the present invention relates to the treatment and prevention of skin autoimmune diseases including but not limited to psoriasis, lupus, vitiligo, scleroderma, dermatomyositis, epidermolysis bullosa, bullous pemphigoid, leukoderma, dermatitis, Koebner's phenomenon and any other skin disease.

The present invention is also directed towards the preparation of a pharmaceutical composition comprising an effective amount of one or more of the said compounds and a pharmaceutically acceptable carrier further adapted to be administered by any suitable mode of administration including oral, parenteral, rectal, topical, intranasal, intravenous, transdermal, sublingual, intramuscular, subcutaneous, ocular and any other local mode of administration.

The present invention discloses compounds of formula I that are useful for treatment and prevention of ER stress related diseases. The compounds of the present invention can be used by way of a formulation or a composition for therapeutics as well as prophylactic applications for the treatment of ER stress related diseases via all modes of administration.

For example, it is suitable for oral, parenteral, rectal, topical, intranasal, intravenous, transdermal, sublingual, intramuscular, subcutaneous, ocular and any other local mode of administration.

The compositions comprising an effective amount of the compounds of formula (I) as active ingredients are intended to be administered by any suitable route including oral, parenteral, rectal, topical, intranasal, intravenous, transdermal, sublingual, intramuscular, subcutaneous, ocular and any other local mode of administration. They may also be typically formulated and administered in unit dosage forms such as tablets, capsule, pills, powders, granules, sterile parenteral solutions or suspensions and oral solutions or suspensions, injections, syrup, liquid, microemulsion, topical creams, ointments, suppositories, sachets, troches and lozenges and oil-water emulsions containing suitable quantities of the compounds of formula I or multiple dosage forms.

Suitable pharmaceutical preparations may also be prepared such as tablets, capsule, pills, powders, granules, sustained release formulations or elixirs for oral administration or in sterile solutions or suspensions for any suitable mode of administration as well as transdermal patch preparation and dry powder inhalers.

An embodiment of the present invention is directed towards treatment of the subject displaying symptoms of ER stress related diseases, comprising steps of administering a therapeutically effective amount of one or more of the compounds of general formula I, their stereoisomers (diastereoisomers, enantiomers), pure or mixed, racemic mixtures, geometrical isomers, tautomers, pharmaceutically acceptable salts, hydrates, solvates, solid forms and mixtures thereof.

Another embodiment of the present invention is directed towards treatment of autoimmune diseases of skin, by reducing stress mediated cell death, comprising steps of administering a therapeutically effective amount of one or more of the compounds of general formula I, their stereoisomers (diastereoisomers, enantiomers), pure or mixed, racemic mixtures, geometrical isomers, tautomers, pharmaceutically acceptable salts, hydrates, solvates, solid forms and mixtures thereof.

Another embodiment of the present invention is directed towards the treatment of skin autoimmune diseases particularly, by reducing the autoimmune mediated cell death of melanocytes, comprising administering a therapeutically effective amount of a pharmaceutical composition or formulation comprising essentially one or more of the compounds of general formula I.

Another embodiment of the present invention is directed towards a method of treating a subject who has developed vitiligo, with a pharmaceutically effective amount of the compounds of general formula I and their stereoisomers (diastereoisomers, enantiomers), pure or mixed, racemic mixtures, geometrical isomers, tautomers, pharmaceutically acceptable salts, hydrates, solvates, solid forms and mixtures thereof.

The present invention envisages treatment of autoimmune diseases by administering the compounds of formula (I) by way of a pharmaceutical composition comprising an effective amount of the compounds along with a pharmaceutically acceptable carrier.

The present invention further envisages the process of preparation of a pharmaceutical composition comprising an effective amount of the compounds along with a pharmaceutically acceptable carrier. Particularly, a further embodiment of the present invention is directed to the preparation of a pharmaceutical composition comprising an effective amount of the compounds along with a pharmaceutically acceptable carrier further adapted to be administered by any suitable mode of administration including oral, parenteral, rectal, topical, intranasal, intravenous, transdermal, sublingual, intramuscular, subcutaneous, ocular and any other local mode of administration.

The present invention envisages application of the compounds of general formula I and their stereoisomers (diastereoisomers, enantiomers), pure or mixed, racemic mixtures, geometrical isomers, tautomers, pharmaceutically acceptable salts, hydrates, solvates, solid forms and mixtures thereof in any process including medicinal, prophylactic, curative, diagnostic, therapeutic or surgical in order to prevent or treat ER stress related diseases.

The present invention also envisages the application of the compounds of general formula I or their physiologically acceptable salts, and still further their stereoisomers (diastereoisomers, enantiomers), pure or mixed, racemic mixtures, geometrical isomers, tautomers, pharmaceutically acceptable salts, hydrates, solvates, solid forms and mixtures thereof, to effect prophylactic or maintenance therapy in a subject who have been treated for such disease and undergone disease regression.

A preferred embodiment of the present invention is directed towards compounds of formula I as provided below:

2-(2-(4-chlorophenyl)-1H-imidazol-4-yl)-N-(4-fluorophenethyl)acetamide;
N-(2-(2-(4-chlorophenyl)-1H-imidazol-4-yl)ethyl)butyramide;
2-(2-(4-chlorophenyl)-1H-imidazol-4-yl)-N-(2-morpholinoethyl)acetamide;
N-butyl-2-(2-(4-chlorophenyl)-1H-imidazol-4-yl)acetamide;
N-butyl-2-(2-(4-chlorophenyl)-1-methyl-1H-imidazol-4-yl)acetamide;
2-(2-(4-chlorophenyl)-1-methy 1-1H-imidazol-4-yl)-N-(2-morpholino ethyl)acetamide;
2-(2-(4-chlorophenyl)-1-methyl-1H-imidazol-4-yl)-N-(3-(trifluoromethyl)phenyl)acetamide;
2-(2-(4-chlorophenyl)-1-methyl-1H-imidazol-4-yl)-N-(3-isopropoxyl)propyl)acetamide;
2-(2-(4-chlorophenyl)-1H-imidazol-4-yl)-N-(3-(trifluoromethyl)phenyl)acetamide;
2-(2-(4-chlorophenyl)-1H-imidazol-4-yl)-N-(3-isopropoxyl)propyl)acetamide;
2-(2-(4-chlorophenyl)-1H-imidazol-4-yl)-N-(4-fluorophenyl)acetamide;
2-(2-(4-chlorophenyl)-1H-imidazol-4-yl)-1-(4,4-difluoropiperidin-1-yl)ethan-1-one;
2-(2-(4-chlorophenyl)-1-methyl-1H-imidazol-4-yl)-N-(4-fluorophenyl)acetamide;
2-(2-(4-chlorophenyl)-1H-imidazol-4-yl)-N-(4-(trifluoromethyl)phenyl)acetamide;
2-(2-(4-chlorophenyl)-1-methyl-1H-imidazol-4-yl)-N-(4-(trifluoromethyl)phenyl)acetamide;
2-(2-(4-chlorophenyl)-1H-imidazol-4-yl)-1-(pyrrolidin-1-yl)ethan-1-one;
2-(2-(4-chlorophenyl)-1-methyl-1H-imidazol-4-yl)-1-(pyrrolidin-1-yl)ethan-1-one;
2-(2-(4-chlorophenyl)-1-methyl-1H-imidazol-4-yl)-N-cyclopentylacetamide;
2-(2-(4-chlorophenyl)-1H-imidazol-4-yl)-N-cyclopentylacetamide;
2-(2-(4-chlorophenyl)-1H-imidazol-4-yl)-1-(4-methylpiperazin-1-yl)ethan-1-one;
2-(2-(4-chlorophenyl)-1-methyl-1H-imidazol-4-yl)-1-(4-methylpiperazin-1-yl)ethan-1-one;
2-(2-(4-chlorophenyl)-1-methy 1-1H-imidazol-4-yl)-N-(4-fluorophenethyl)acetamide;
2-(2-(4-chlorophenyl)-1H-imidazol-4-yl)-1-morpholinoethan-1-one;
2-(2-(4-chlorophenyl)-1H-imidazol-4-yl)-1-thiomorpholinoethan-1-one;
N-(2-(2-(4-chlorophenyl)-1H-imidazol-4-yl)ethyl)-3,3-dimethylbutanamide;
N-(2-(2-(4-chlorophenyl)-1H-imidazol-4-yl)ethyl)-2,2-dimethylbutanamide;
N-(2-(2-(4-chlorophenyl)-1H-imidazol-4-yl)ethyl)-3-methylbutanamide;
N-(2-(2-phenyl-1H-imidazol-4-yl)ethyl)buty ramide;
N-(2-(2-(3-(1H-pyrazol-1-yl)phenyl)-1H-imidazol-4-yl)ethyl)butyramide;
N-(2-(2-(4-methoxy phenyl)-1H-imidazol-4-yl)ethyl)buty ramide;
N-(2-(2-(4-phenoxyphenyl)-1H-imidazol-4-yl)ethyl)butyramide;
N-(2-(2-(pyridin-4-yl)-1H-imidazol-4-yl)ethyl)butyramide;
N-(2-(1-methyl-2-(pyridin-4-yl)-1H-imidazol-4-yl)ethyl)butyramide;
N-(2-(2-(3-(1H-pyrrol-2-yl)phenyl)-1H-imidazol-4-yl)ethyl)butyramide;
N-(2-(2-(p-tolyl)-1H-imidazol-4-yl)ethyl)butyramide;
N-(2-(2-(3,5-dichlorophenyl)-1H-imidazol-4-yl)ethyl)butyramide;
N-(2-(2-([1,1'-biphenyl]-3-yl)-1H-imidazol-4-yl)ethyl)butyramide;
N-(2-(2-(4-vinylphenyl)-1H-imidazol-4-yl)ethyl)buty ramide;
N-(2-(2-(3-(1H-pyrrol-2-yl)phenyl)-1-methyl-1H-imidazol-4-yl)ethyl)butyramide;
N-(2-(2-(3-morpholinophenyl)-1H-imidazol-4-yl)ethyl) buty ramide;
N-(2-(2-(3-(piperidin-1-yl)phenyl)-1H-imidazol-4-yl)ethyl)butyramide;
N-(2-(2-(3-(pyrimidin-5-yl)phenyl)-1H-imidazol-4-yl)ethyl)butyramide;
N-(2-(2-(4-fluorophenyl)-1H-imidazol-4-yl)ethyl)butyramide;
N-(2-(2-(4-benzylphenyl)-1H-imidazol-4-yl)ethyl)butyramide;
N-(2-(1-methyl-2-(3-morpholinophenyl)-1H-imidazol-4-yl)ethyl)butyramide;
N-(2-(2-(4-chlorophenyl)-1H-imidazol-4-yl)ethyl)cyclopropanecarboxamide;
N-(2-(2-(4-chlorophenyl)-1H-imidazol-4-yl)ethyl)-4,4,4-trifluorobutanamide;
N-(2-(2-(4-chlorophenyl)-1H-imidazol-4-yl)ethyl)acetamide;
N-(2-(2-(4-chlorophenyl)-1H-imidazol-4-yl)ethyl)-2-methoxyacetamide;
N-(2-(2-(4-chlorophenyl)-1H-imidazol-4-yl)ethyl)cyclobutanecarboxamide;
N-(2-(2-(4-chlorophenyl)-1H-imidazol-4-yl)ethyl)-4-fluorobenzamide;

2-((1,S,4R)-bicyclo[2.2.1]heptan-2-yl-N-(2-(4-chlorophenyl)-1H-imidazol-4-yl)acetamide;
N-(2-(2-(4-chlorophenyl)-1H-imidazol-4-yl)ethyl)-4-(trifluoromethyl)benzamide;
N-(2-(2-(4-chlorophenyl)-1H-imidazol-4-yl)ethyl)-3,5-difluorobenzamide;
N-(2-(2-(4-chlorophenyl)-1H-imidazol-4-yl)ethyl)cyclopent-1-ene-1-carboxamide;
N-(2-(2-(2,3-dihydrobenzo[b][1,4]dioxin-6-yl)-1H-imidazol-4-yl)ethyl)cyclopent-1-ene-1-carboxamide;
N-(2-(2-(benzo[d][1,3]dioxol-5-yl)-1H-imidazol-4-yl)ethyl)cyclopent-1-ene-1-carboxamide;
(3r,5r,7r)-N-(2-(2-(4-chlorophenyl)-1H-imidazol-4-yl)ethyl)adamantane-1-carboxamide;
N-(2-(2-(4-chlorophenyl)-1H-imidazol-4-yl)ethyl)-4-methyl-2-(pyridin-2-yl)thiazole-5-carboxamide;
N-(2-(2-(2,4-dichlorophenyl)-1H-imidazol-4-yl)ethyl)-4-(trifluoromethyl)benzamide;
N-(2-(2-(4-chlorophenyl)-1H-imidazol-4-yl)ethyl)hexanamide;
N-(2-(2-(4-chlorophenyl)-1H-imidazol-4-yl)ethyl)octanamide;
N-(2-(2-(3,5-dichlorophenyl)-1H-imidazol-4-yl)ethyl)-3,5-difluorobenzamide;
N-(2-(2-(2,4-dichlorophenyl)-1H-imidazol-4-yl)ethyl)-4-fluorobenzamide;
N-(2-(2-(2,4-dichlorophenyl)-1H-imidazol-4-yl)ethyl)-3,5-difluorobenzamide;
N-(2-(2-(4-chlorophenyl)-1H-imidazol-4-yl)ethyl)-2-(4-(trifluoromethyl)phenyl)acetamide;
N-(2-(2-(4-chlorophenyl)-1H-imidazol-4-yl)ethyl)-3-(4-(trifluoromethyl)phenyl)propenamide;
N-(2-(2-(4-chlorophenyl)-1H-imidazol-4-yl)ethyl)-2-(4-fluorophenyl)acetamide;
N-(2-(2-(4-chlorophenyl)-1H-imidazol-4-yl)ethyl)-3-(4-fluorophenyl)propenamide;
N-(2-(2-(4-chlorophenyl)-1H-imidazol-4-yl)ethyl)-2-(3,5-difluorophenyl)acetamide;
N-(2-(2-(4-chlorophenyl)-1H-imidazol-4-yl)ethyl)-3-(3,5-difluorophenyl)propenamide;

Without limiting the scope of the invention, another advantageous embodiment of the present invention is directed towards preferred compounds chosen from among the following:

| Compound No. | Structure | IUPAC Name |
|---|---|---|
| 001 | 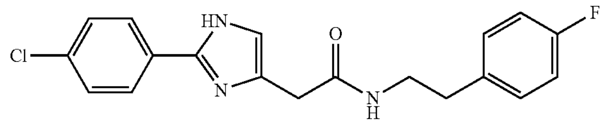 [SMILES: O=C(Cc1c[nH]c(-c2ccc(Cl)cc2)n1)NCCc1ccc(F)cc1] | 2-(2-(4-chlorophenyl)-1H-imidazol-4-yl)-N-(4-fluorophenethyl)acetamide |
| 002 | 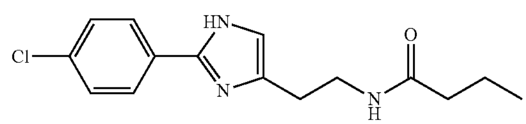 [SMILES: CCCC(=O)NCCc1c[nH]c(-c2ccc(Cl)cc2)n1] | N-(2-(2-(4-chlorophenyl)-1H-imidazol-4-yl)ethyl)butyramide |
| 003 | 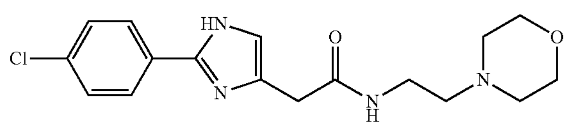 [SMILES: O=C(Cc1c[nH]c(-c2ccc(Cl)cc2)n1)NCCN1CCOCC1] | 2-(2-(4-chlorophenyl)-1H-imidazol-4-yl)-N-(2-morpholinoethyl)acetamide |
| 004 | 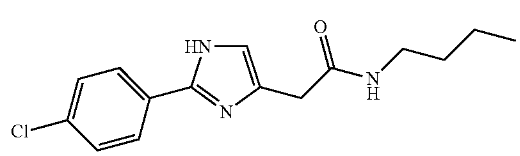 [SMILES: CCCCNC(=O)Cc1c[nH]c(-c2ccc(Cl)cc2)n1] | N-butyl-2-(2-(4-chlorophenyl)-1H-imidazol-4-yl)acetamide |
| 005 | 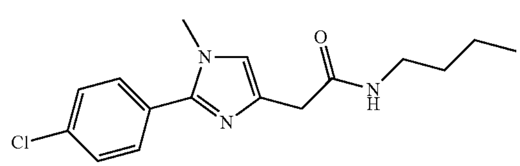 [SMILES: CCCCNC(=O)Cc1cn(C)c(-c2ccc(Cl)cc2)n1] | N-butyl-2-(2-(4-chlorophenyl)-1-methyl-1H-imidazol-4-yl)acetamide |
| 006 | 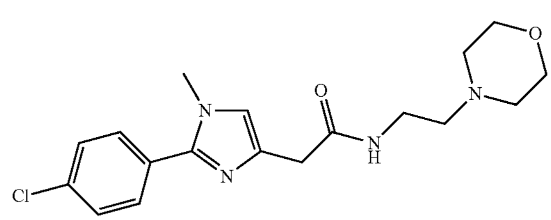 [SMILES: Cn1cc(CC(=O)NCCN2CCOCC2)nc1-c1ccc(Cl)cc1] | 2-(2-(4-chlorophenyl)-1-methyl-1H-imidazol-4-yl)-N-(2-morpholinoethyl)acetamide |

-continued

| Compound No. | Structure | IUPAC Name |
| --- | --- | --- |
| 007 | 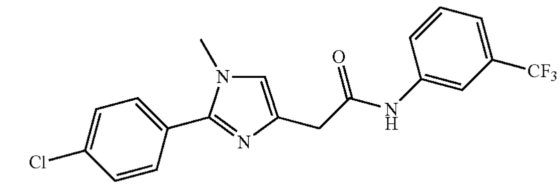 [SMILES: Cn1cc(CC(=O)Nc2cccc(C(F)(F)F)c2)nc1-c1ccc(Cl)cc1] | 2-(2-(4-chlorophenyl)-1-methyl-1H-imidazol-4-yl)-N-(3-(trifluoromethyl)phenyl)acetamide |
| 008 | 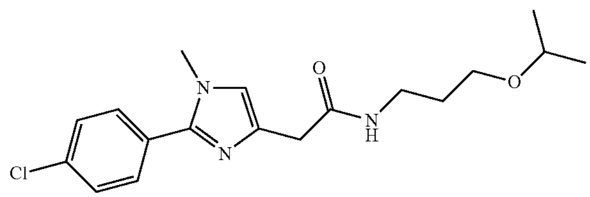 [SMILES: CC(C)OCCCNC(=O)Cc1cn(C)c(-c2ccc(Cl)cc2)n1] | 2-(2-(4-chlorophenyl)-1-methyl-1H-imidazol-4-yl)-N-(3-isopropoxypropyl)acetamide |
| 009 | 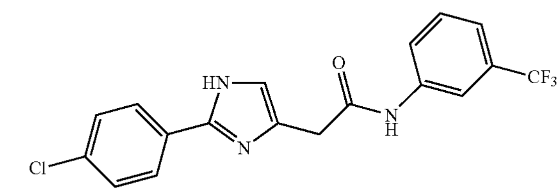 [SMILES: O=C(Cc1c[nH]c(-c2ccc(Cl)cc2)n1)Nc1cccc(C(F)(F)F)c1] | 2-(2-(4-chlorophenyl)-1H-imidazol-4-yl)-N-(3-(trifluoromethyl)phenyl)acetamide |
| 010 | 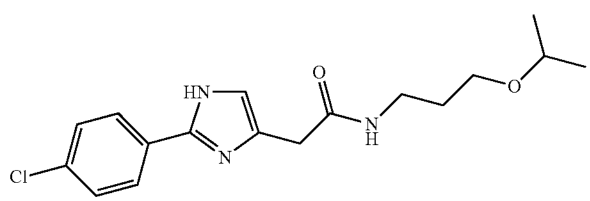 [SMILES: CC(C)OCCCNC(=O)Cc1c[nH]c(-c2ccc(Cl)cc2)n1] | 2-(2-(4-chlorophenyl)-1H-imidazol-4-yl)-N-(3-isopropoxypropyl)acetamide |
| 011 | 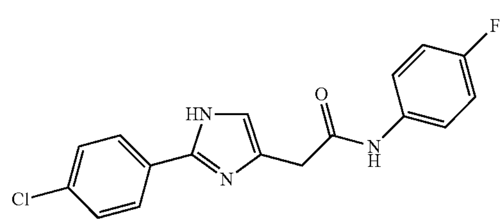 [SMILES: O=C(Cc1c[nH]c(-c2ccc(Cl)cc2)n1)Nc1ccc(F)cc1] | 2-(2-(4-chlorophenyl)-1H-imidazol-4-yl)-N-(4-fluorophenyl)acetamide |
| 012 | 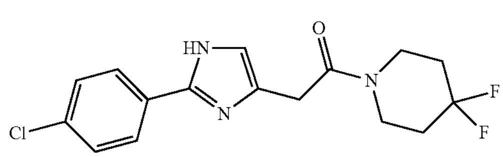 [SMILES: O=C(Cc1c[nH]c(-c2ccc(Cl)cc2)n1)N1CCC(F)(F)CC1] | 2-(2-(4-chlorophenyl)-1H-imidazol-4-yl)-1-(4,4-difluoropiperidin-1-yl)ethan-1-one |
| 013 | 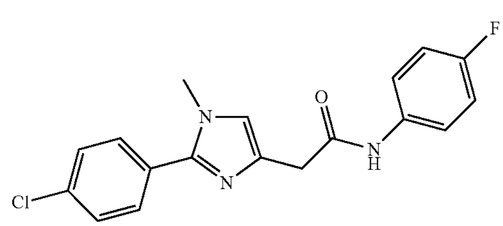 [SMILES: Cn1cc(CC(=O)Nc2ccc(F)cc2)nc1-c1ccc(Cl)cc1] | 2-(2-(4-chlorophenyl)-1-methyl-1H-imidazol-4-yl)-N-(4-fluorophenyl)acetamide |
| 014 | 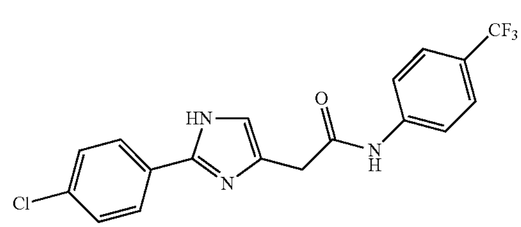 [SMILES: O=C(Cc1c[nH]c(-c2ccc(Cl)cc2)n1)Nc1ccc(C(F)(F)F)cc1] | 2-(2-(4-chlorophenyl)-1H-imidazol-4-yl)-N-(4-(trifluoromethyl)phenyl)acetamide |

| Compound No. | Structure | IUPAC Name |
| --- | --- | --- |
| 015 | 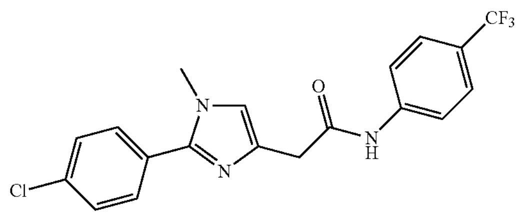 [SMILES: Cn1cc(CC(=O)Nc2ccc(C(F)(F)F)cc2)nc1-c1ccc(Cl)cc1] | 2-(2-(4-chlorophenyl)-1-methyl-1H-imidazol-4-yl)-N-(4-(trifluoromethyl)phenyl)acetamide |
| 016 | 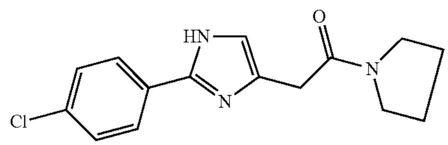 [SMILES: O=C(Cc1c[nH]c(-c2ccc(Cl)cc2)n1)N1CCCC1] | 2-(2-(4-chlorophenyl)-1H-imidazol-4-yl)-1-(pyrrolidin-1-yl)ethan-1-one |
| 017 | 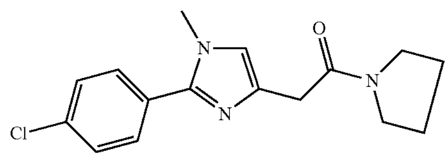 [SMILES: Cn1cc(CC(=O)N2CCCC2)nc1-c1ccc(Cl)cc1] | 2-(2-(4-chlorophenyl)-1-methyl-1H-imidazol-4-yl)-1-(pyrrolidin-1-yl)ethan-1-one |
| 018 | 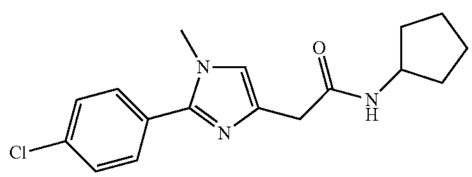 [SMILES: Cn1cc(CC(=O)NC2CCCC2)nc1-c1ccc(Cl)cc1] | 2-(2-(4-chlorophenyl)-1-methyl-1H-imidazol-4-yl)-N-cyclopentylacetamide |
| 019 | 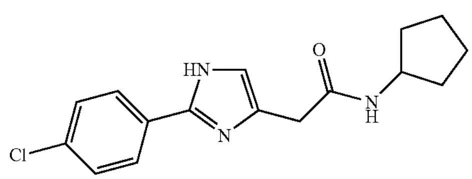 [SMILES: O=C(Cc1c[nH]c(-c2ccc(Cl)cc2)n1)NC1CCCC1] | 2-(2-(4-chlorophenyl)-1H-imidazol-4-yl)-N-cyclopentylacetamide |
| 020 | 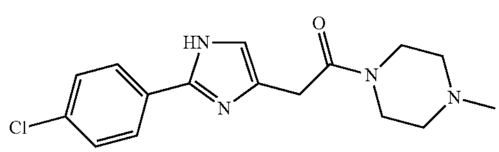 [SMILES: CN1CCN(C(=O)Cc2c[nH]c(-c3ccc(Cl)cc3)n2)CC1] | 2-(2-(4-chlorophenyl)-1H-imidazol-4-yl)-1-(4-methylpiperazin-1-yl)ethan-1-one |
| 021 | 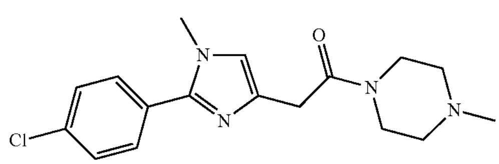 [SMILES: CN1CCN(C(=O)Cc2cn(C)c(-c3ccc(Cl)cc3)n2)CC1] | 2-(2-(4-chlorophenyl)-1-methyl-1H-imidazol-4-yl)-1-(4-methylpiperazin-1-yl)ethan-1-one |
| 022 | 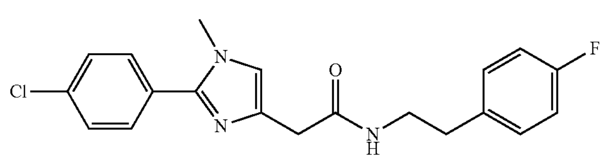 [SMILES: Cn1cc(CC(=O)NCCc2ccc(F)cc2)nc1-c1ccc(Cl)cc1] | 2-(2-(4-chlorophenyl)-1-methyl-1H-imidazol-4-yl)-N-(4-fluorophenethyl)acetamide |
| 023 | 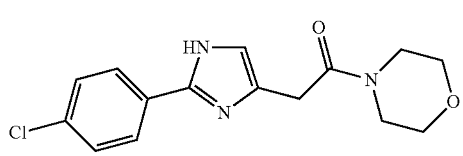 [SMILES: O=C(Cc1c[nH]c(-c2ccc(Cl)cc2)n1)N1CCOCC1] | 2-(2-(4-chlorophenyl)-1H-imidazol-4-yl)-1-morpholinoethan-1-one |

| Compound No. | Structure | IUPAC Name |
|---|---|---|
| 024 | 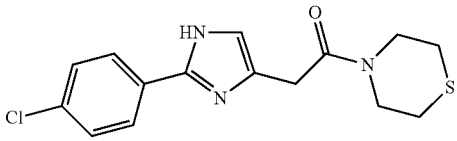 [SMILES: O=C(Cc1c[nH]c(-c2ccc(Cl)cc2)n1)N1CCSCC1] | 2-(2-(4-chlorophenyl)-1H-imidazol-4-yl)-1-thiomorpholinoethan-1-one |
| 025 | 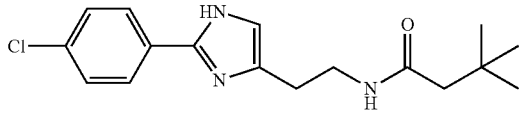 | N-(2-(2-(4-chlorophenyl)-1H-imidazol-4-yl)ethyl)-3,3-dimethylbutanamide |
| 026 | 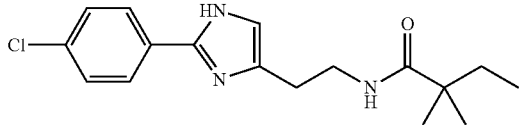 [SMILES: CCC(C)(C)C(=O)NCCc1c[nH]c(-c2ccc(Cl)cc2)n1] | N-(2-(2-(4-chlorophenyl)-1H-imidazol-4-yl)ethyl)-2,2-dimethylbutanamide |
| 027 | 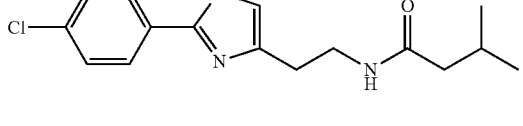 | N-(2-(2-(4-chlorophenyl)-1H-imidazol-4-yl)ethyl)-3-methylbutanamide |
| 028 | 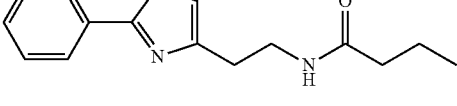 | N-(2-(2-phenyl-1H-imidazol-4-yl)ethyl)butyramide |
| 029 | 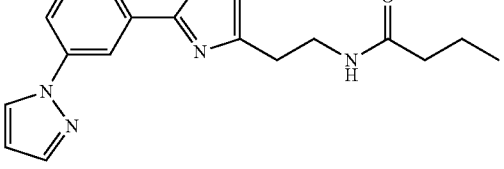 | N-(2-(2-(3-(1H-pyrazol-1-yl)phenyl)-1H-imidazol-4-yl)ethyl)butyramide |
| 030 | 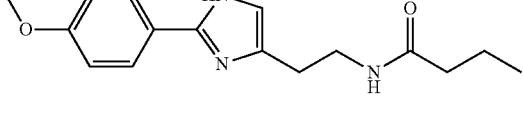 | N-(2-(2-(4-methoxyphenyl)-1H-imidazol-4-yl)ethyl)butyramide |
| 031 | 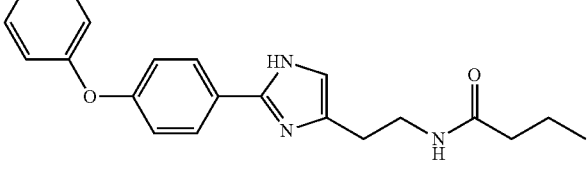 | N-(2-(2-(4-phenoxyphenyl)-1H-imidazol-4-yl)ethyl)butyramide |
| 032 | 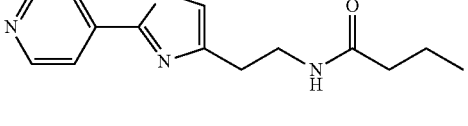 | N-(2-(2-(pyridin-4-yl)-1H-imidazol-4-yl)ethyl)butyramide |
| 033 | 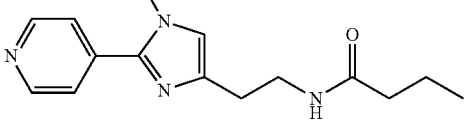 | N-(2-(1-methyl-2-(pyridin-4-yl)-1H-imidazol-4-yl)ethyl)butyramide |

-continued

| Compound No. | Structure | IUPAC Name |
|---|---|---|
| 034 | 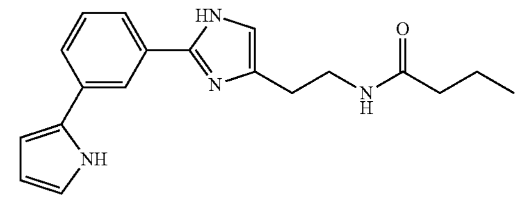 [SMILES: CCCC(=O)NCCc1c[nH]c(-c2cccc(-c3ccc[nH]3)c2)n1] | N-(2-(2-(3-(1H-pyrrol-2-yl)phenyl)-1H-imidazol-4-yl)ethyl)butyramide |
| 035 | 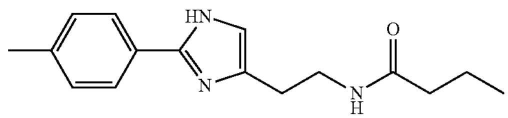 [SMILES: CCCC(=O)NCCc1c[nH]c(-c2ccc(C)cc2)n1] | N-(2-(2-(p-tolyl)-1H-imidazol-4-yl)ethyl)butyramide |
| 036 | 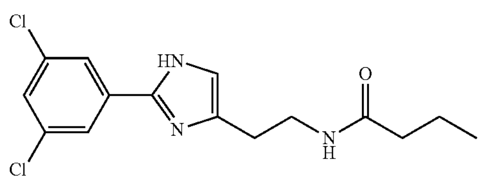 [SMILES: CCCC(=O)NCCc1c[nH]c(-c2cc(Cl)cc(Cl)c2)n1] | N-(2-(2-(3,5-dichlorophenyl)-1H-imidazol-4-yl)ethyl)butyramide |
| 037 | 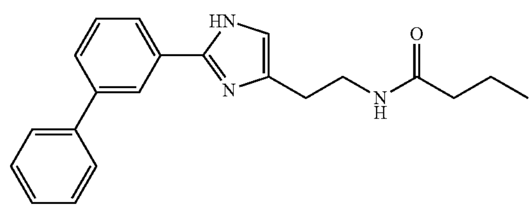 [SMILES: CCCC(=O)NCCc1c[nH]c(-c2cccc(-c3ccccc3)c2)n1] | N-(2-(2-([1,1'-biphenyl]-3-yl)-1H-imidazol-4-yl)ethyl)butyramide |
| 038 | 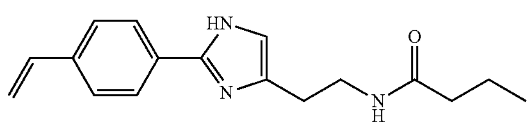 [SMILES: C=Cc1ccc(-c2nc(CCNC(=O)CCC)c[nH]2)cc1] | N-(2-(2-(4-vinylphenyl)-1H-imidazol-4-yl)ethyl)butyramide |
| 039 | 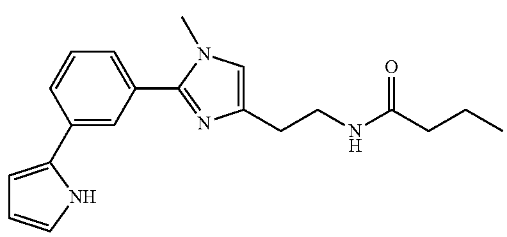 [SMILES: CCCC(=O)NCCc1cn(C)c(-c2cccc(-c3ccc[nH]3)c2)n1] | N-(2-(2-(3-(1H-pyrrol-2-yl)phenyl)-1-methyl-1H-imidazol-4-yl)ethyl)butyramide |
| 040 | 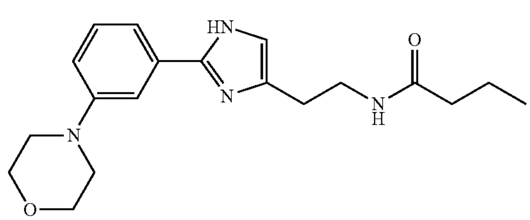 [SMILES: CCCC(=O)NCCc1c[nH]c(-c2cccc(N3CCOCC3)c2)n1] | N-(2-(2-(3-morpholinophenyl)-1H-imidazol-4-yl)ethyl)butyramide |
| 041 | 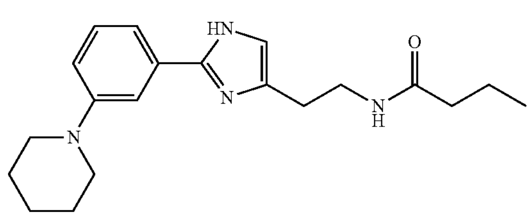 [SMILES: CCCC(=O)NCCc1c[nH]c(-c2cccc(N3CCCCC3)c2)n1] | N-(2-(2-(3-(piperidin-1-yl)phenyl)-1H-imidazol-4-yl)ethyl)butyramide |

-continued

| Compound No. | Structure | IUPAC Name |
|---|---|---|
| 042 | 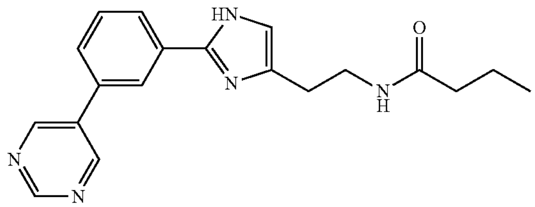 [SMILES: CCCC(=O)NCCc1c[nH]c(-c2cccc(-c3cncnc3)c2)n1] | N-(2-(2-(3-(pyrimidin-5-yl)phenyl)-1H-imidazol-4-yl)ethyl)butyramide |
| 043 | 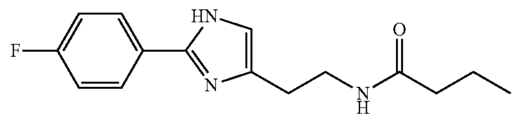 [SMILES: CCCC(=O)NCCc1c[nH]c(-c2ccc(F)cc2)n1] | N-(2-(2-(4-fluorophenyl)-1H-imidazol-4-yl)ethyl)butyramide |
| 044 | 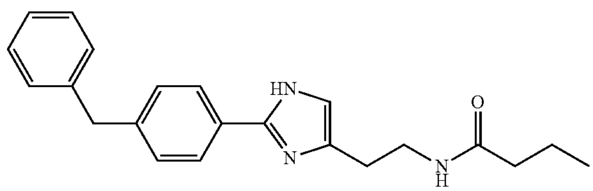 [SMILES: CCCC(=O)NCCc1c[nH]c(-c2ccc(Cc3ccccc3)cc2)n1] | N-(2-(2-(4-benzylphenyl)-1H-imidazol-4-yl)ethyl)butyramide |
| 045 | 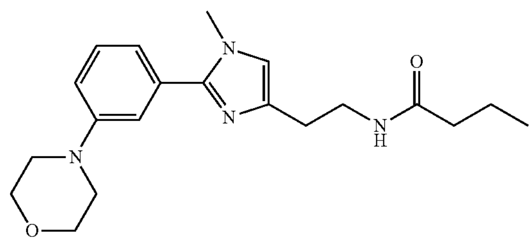 [SMILES: CCCC(=O)NCCc1cn(C)c(-c2cccc(N3CCOCC3)c2)n1] | N-(2-(1-methyl-2-(3-morpholinophenyl)-1H-imidazol-4-yl)ethyl)butyramide |
| 046 | 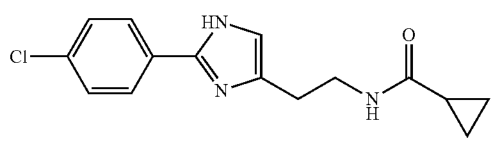 [SMILES: O=C(NCCc1c[nH]c(-c2ccc(Cl)cc2)n1)C1CC1] | N-(2-(2-(4-chlorophenyl)-1H-imidazol-4-yl)ethyl)cyclopropanecarboxamide |
| 047 | 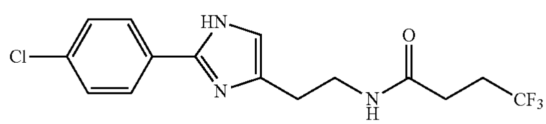 [SMILES: O=C(CCC(F)(F)F)NCCc1c[nH]c(-c2ccc(Cl)cc2)n1] | N-(2-(2-(4-chlorophenyl)-1H-imidazol-4-yl)ethyl)-4,4,4-trifluorobutanamide |
| 048 | 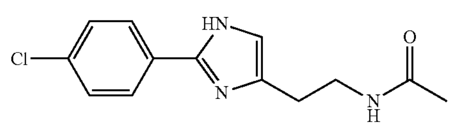 [SMILES: CC(=O)NCCc1c[nH]c(-c2ccc(Cl)cc2)n1] | N-(2-(2-(4-chlorophenyl)-1H-imidazol-4-yl)ethyl)acetamide |
| 049 | 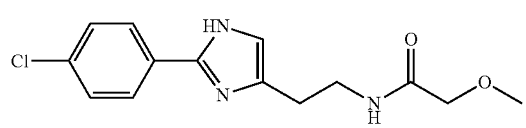 | N-(2-(2-(4-chlorophenyl)-1H-imidazol-4-yl)ethyl)-2-methoxyacetamide |
| 050 | 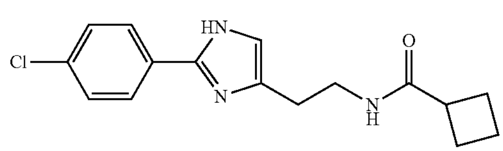 [SMILES: O=C(NCCc1c[nH]c(-c2ccc(Cl)cc2)n1)C1CCC1] | N-(2-(2-(4-chlorophenyl)-1H-imidazol-4-yl)ethyl)cyclobutanecarboxamide |

| Compound No. | Structure | IUPAC Name |
|---|---|---|
| 051 | 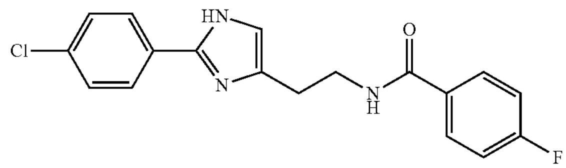 [SMILES: O=C(NCCc1c[nH]c(-c2ccc(Cl)cc2)n1)c1ccc(F)cc1] | N-(2-(2-(4-chlorophenyl)-1H-imidazol-4-yl)ethyl)-4-fluorobenzamide |
| 052 | 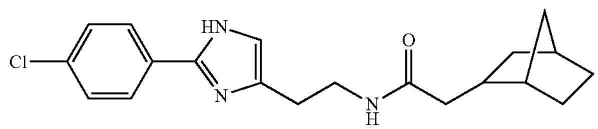 [SMILES: O=C(CC1CC2CCC1C2)NCCc1c[nH]c(-c2ccc(Cl)cc2)n1] | 2-((1S,4R)-bicyclo[2.2.1]heptan-2-yl-N-(2-(4-chlorophenyl)-1H-imidaazol-4-yl)acetamide |
| 053 | 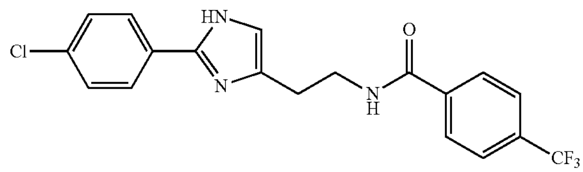 [SMILES: O=C(NCCc1c[nH]c(-c2ccc(Cl)cc2)n1)c1ccc(C(F)(F)F)cc1] | N-(2-(2-(4-chlorophenyl)-1H-imidazol-4-yl)ethyl)-4-(trifluoromethyl)benzamide |
| 054 | 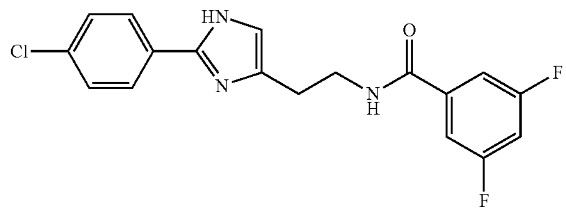 [SMILES: O=C(NCCc1c[nH]c(-c2ccc(Cl)cc2)n1)c1cc(F)cc(F)c1] | N-(2-(2-(4-chlorophenyl)-1H-imidazol-4-yl)ethyl)-3,5-difluorobenzamide |
| 055 | 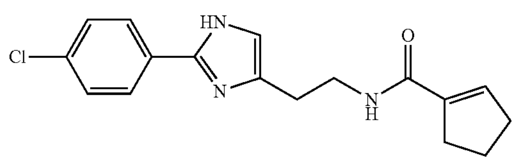 [SMILES: O=C(NCCc1c[nH]c(-c2ccc(Cl)cc2)n1)C1=CCCC1] | N-(2-(2-(4-chlorophenyl)-1H-imidazol-4-yl)ethyl)cyclopent-1-ene-1-carboxamide |
| 056 | 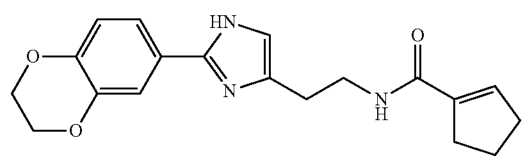 [SMILES: O=C(NCCc1c[nH]c(-c2ccc3c(c2)OCCO3)n1)C1=CCCC1] | N-(2-(2-(2,3-dihydrobenzo[b][1,4]dioxin-6-yl)-1H-imidazol-4-yl)ethyl)cyclopent-1-ene-1-carboxamide |
| 057 | 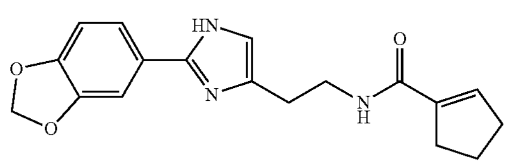 [SMILES: O=C(NCCc1c[nH]c(-c2ccc3c(c2)OCO3)n1)C1=CCCC1] | N-(2-(2-(benzo[d][1,3]dioxol-5-yl)-1H-imidazol-4-yl)ethyl)cyclopent-1-ene-1-carboxamide |
| 058 | 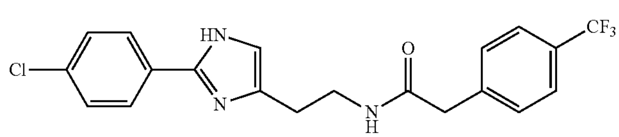 [SMILES: O=C(Cc1ccc(C(F)(F)F)cc1)NCCc1c[nH]c(-c2ccc(Cl)cc2)n1] | N-(2-(2-(4-chlorophenyl)-1H-imidazol-4-yl)ethyl)-2-(4-(trifluoromethyl)phenyl)acetamide |
| 059 | 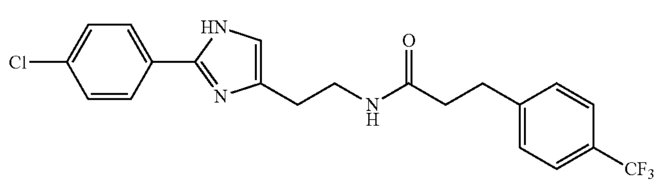 [SMILES: O=C(CCc1ccc(C(F)(F)F)cc1)NCCc1c[nH]c(-c2ccc(Cl)cc2)n1] | N-(2-(2-(4-chlorophenyl)-1H-imidazol-4-yl)ethyl)-3-(4-(trifluoromethyl)phenyl)propanamide |

| Compound No. | Structure | IUPAC Name |
| --- | --- | --- |
| 060 | 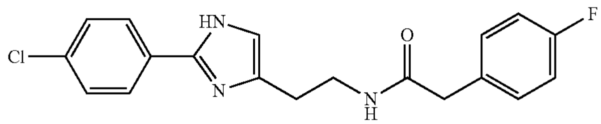 [SMILES: O=C(Cc1ccc(F)cc1)NCCc1c[nH]c(-c2ccc(Cl)cc2)n1] | N-(2-(2-(4-chlorophenyl)-1H-imidazol-4-yl)ethyl)-2-(4-fluorophenyl)acetamide |
| 061 | 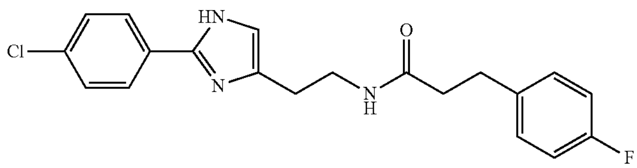 [SMILES: O=C(CCc1ccc(F)cc1)NCCc1c[nH]c(-c2ccc(Cl)cc2)n1] | N-(2-(2-(4-chlorophenyl)-1H-imidazol-4-yl)ethyl)-3-(4-fluorophenyl)propanamide |
| 062 | 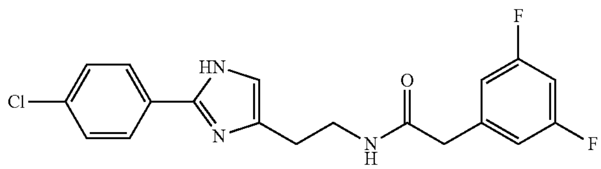 [SMILES: O=C(Cc1cc(F)cc(F)c1)NCCc1c[nH]c(-c2ccc(Cl)cc2)n1] | N-(2-(2-(4-chlorophenyl)-1H-imidazol-4-yl)ethyl)-2-(3,5-difluorophenyl)acetamide |
| 063 | 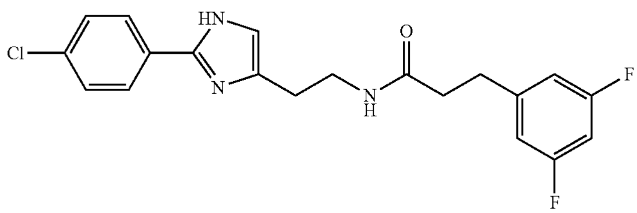 [SMILES: O=C(CCc1cc(F)cc(F)c1)NCCc1c[nH]c(-c2ccc(Cl)cc2)n1] | N-(2-(2-(4-chlorophenyl)-1H-imidazol-4-yl)ethyl)-3-(3,5-difluorophenyl)propanamide |
| 064 | 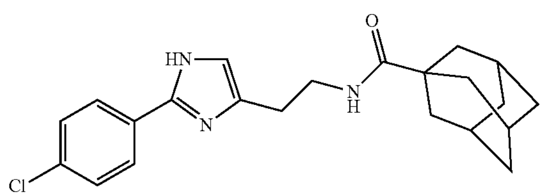 [SMILES: O=C(NCCc1c[nH]c(-c2ccc(Cl)cc2)n1)C12CC3CC(CC(C3)C1)C2] | (3r,5r,7r)-N-(2-(2-(4-chlorophenyl)-1H-imidazol-4-yl)ethyl)adamantane-1-carboxamide |
| 065 | 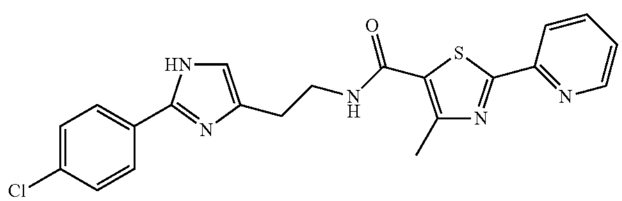 [SMILES: Cc1nc(-c2ccccn2)sc1C(=O)NCCc1c[nH]c(-c2ccc(Cl)cc2)n1] | N-(2-(2-(4-chlorophenyl)-1H-imidazol-4-yl)ethyl)-4-methyl-2-(pyridin-2-yl)thiazole-5-carboxamide |
| 066 | 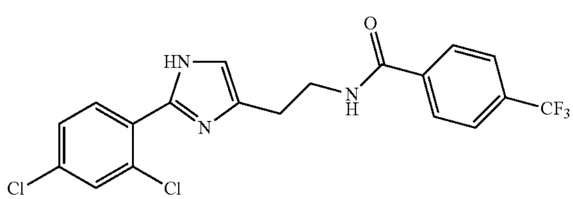 [SMILES: O=C(NCCc1c[nH]c(-c2ccc(Cl)cc2Cl)n1)c1ccc(C(F)(F)F)cc1] | N-(2-(2-(2,4-dichlorophenyl)-1H-imidazol-4-yl)ethyl)-4-(trifluoromethyl)benzamide |
| 067 | 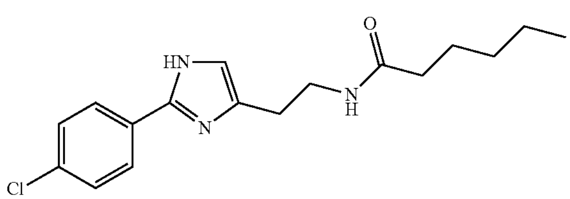 [SMILES: CCCCCC(=O)NCCc1c[nH]c(-c2ccc(Cl)cc2)n1] | N-(2-(2-(4-chlorophenyl)-1H-imidazol-4-yl)ethyl)hexanamide |

| Compound No. | Structure | IUPAC Name |
| --- | --- | --- |
| 068 | 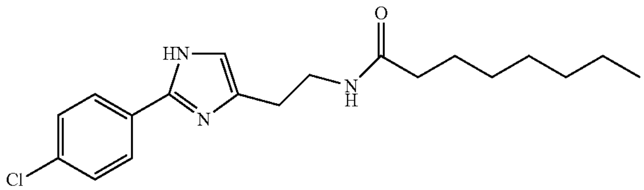 [SMILES: CCCCCCCC(=O)NCCc1c[nH]c(-c2ccc(Cl)cc2)n1] | N-(2-(2-(4-chlorophenyl)-1H-imidazol-4-yl)ethyl)octanamide |
| 069 | 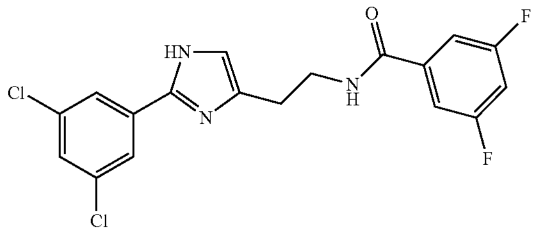 [SMILES: O=C(NCCc1c[nH]c(-c2cc(Cl)cc(Cl)c2)n1)c1cc(F)cc(F)c1] | N-(2-(2-(3,5-dichlorophenyl)-1H-imidazol-4-yl)ethyl)-3,5-difluorobenzamide |
| 070 | 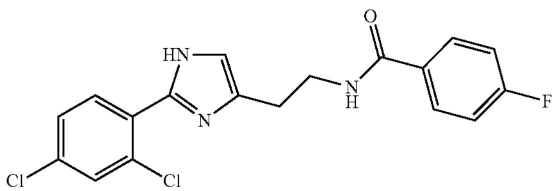 [SMILES: O=C(NCCc1c[nH]c(-c2ccc(Cl)cc2Cl)n1)c1ccc(F)cc1] | N-(2-(2-(2,4-dichlorophenyl)-1H-imidazol-4-yl)ethyl)-4-fluorobenzamide |
| 071 | 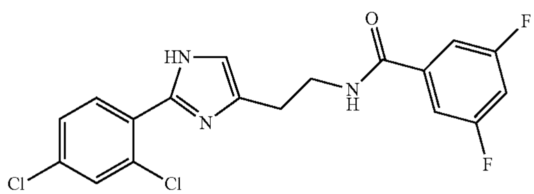 [SMILES: O=C(NCCc1c[nH]c(-c2ccc(Cl)cc2Cl)n1)c1cc(F)cc(F)c1] | N-(2-(2-(2,4-dichlorophenyl)-1H-imidazol-4-yl)ethyl)-3,5-difluorobenzamide |

The present invention further describes novel and inventive process for the preparation of the compounds of the present invention. The compounds of formula I have been synthesized by novel and inventive processes having general scheme as given below:

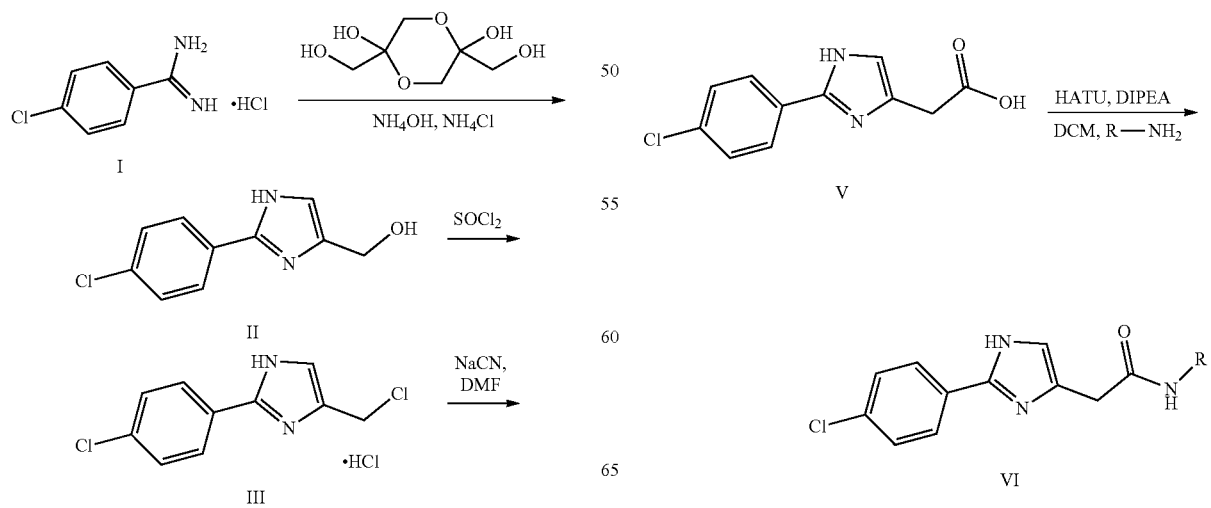

Scheme I

Procedure A:

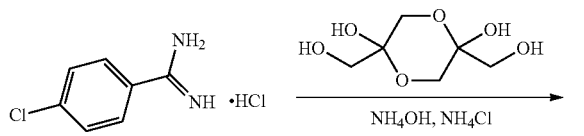

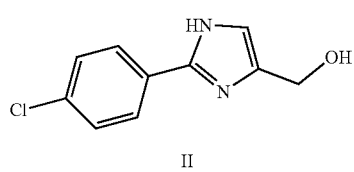

Synthesis of compound II: (3.15 g, 49%) (2-(4-chlorophenyl)-1H-imidazol-4-yl)methanol: To the stirred solution of 4-chlorobenzamidine hydrochloride (0.19 mol) and NH₄Cl (54 g) in NH₄OH (380 ml), 1,3 dihydroxyacetone dimer (0.40 mol) was added at RT and reaction was stirred for half hour at reflux condition, cooled reaction mass, filter through Buckner funnel, solid was washed with diethyl ether (40 ml) two times and dried well.

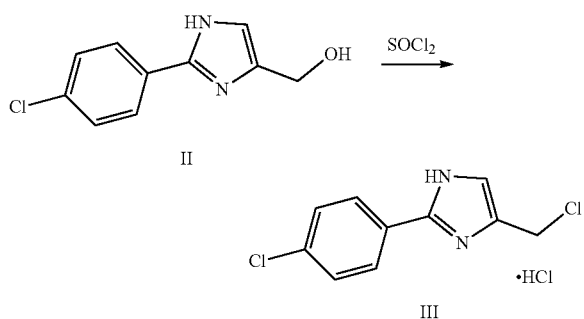

Synthesis of compound III: (4.8 g, 89%)4-(chloromethyl)-2-(4-chlorophenyl)-1H-imidazole.HCl: To the stirred solution of II (0.023 mol) and SOCl₂ (0.23 mol) was refluxed for 2 h. then mixture was concentrated and washed with diethyl ether (30 ml) and dried well.

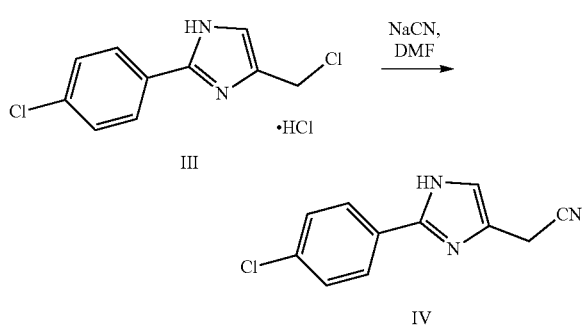

Synthesis of compound IV: (1.54 g, 55%) 2-(2-(4-chlorophenyl)-1H-imidazol-4-yl)acetonitrile: To the stirred solution of DMF (30 ml) and free salt (by using sodium bicarbonate) of compound III (0.013 mol), NaCN (0.015 mol) was added at room temperature and reaction mass was stirred for 12 h. water was added to reaction mass and compound was extracted by using ethyl acetate, organic layer was dried over Na₂SO₄ and concentrated.

Procedure B:

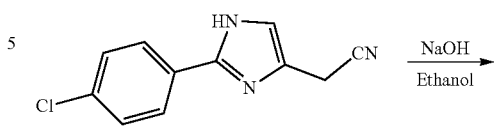

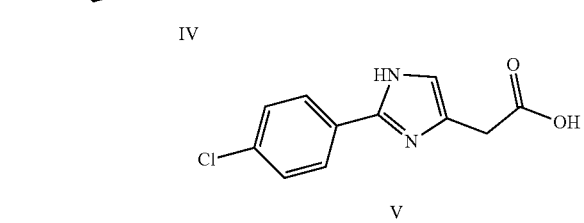

Synthesis of compound V: 2-(2-(4-chlorophenyl)-1H-imidazol-4-yl)acetic acid: To a stirred solution of compound IV (0.0069 mol) in ethanol (30 ml), NaOH (0.0276 mol) and water (10 ml) were added and refluxed for 4 h. Cooled the reaction mixture to room temperature, concentrated and acidify to pH ~3 with conc. HCl. diluted with ethyl acetate. Organic layer was dried over Na₂SO₄ and concentrate.

Procedure C:

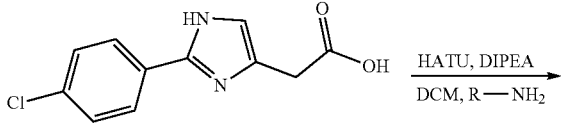

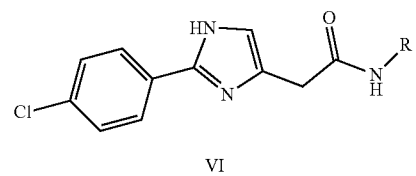

Synthesis of general compound VI:

To the stirred solution of acid (compound V) (0.54 mmol), amine (R—NH₂) (0.33 mmol) and HATU (0.60 mmol) in 4 ml dichloromethane, DIPEA (1.09 mmol) was added at 0° C. and reaction was stirred for overnight. Concentrate reaction mass and diluted with ethyl acetate. Washed with 1N HCl, saturated NaHCo₃ solution, and saturated brine solution. Organic layer was dried over Na₂SO₄, concentrate and purified by column chromatography.

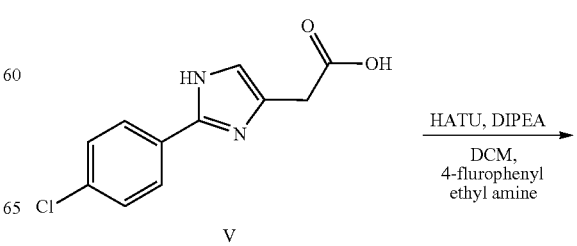

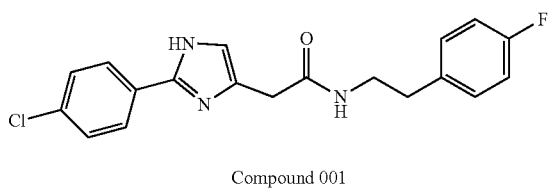

Compound 001

2-(2-(4-chlorophenyl)-1H-imidazol-4-yl)-N-(4-fluorophenethyl)acetamide (001): Compound 001 (66 mg, 35%) was synthesized from compound V by following procedure C. $^1$H NMR (DMSO-d$_6$, 500 MHz): δ 12.43 (s, 1H), 7.89 (t, J=8.4 Hz, 3H), 7.50 (d, J=8.4 Hz, 2H), 7.21 (dd, J=8.3 Hz, 5.9 Hz, 2H), 7.04 (m, 3H), 3.35 (s, 2H), 3.29 (q, J=6.5 Hz, 2H), 2.70 (t, J=6.8 Hz, 2H).

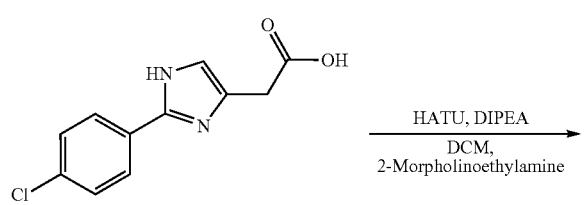

Compound 003

2-(2-(4-chlorophenyl)-1H-imidazol-4-yl)-N-(2-morpholinoethyl) acetamide (Compound 003) Compound 003 (38 mg, 30%) was synthesized from compound V by following procedure C. $^1$H NMR (DMSO-d$_6$, 500 MHz): δ 12.45 (s, 1H), 7.91 (d, 3H), 7.49 (d, 2H), 7.02 (s, 1H), 3.53 (s, 4H), 3.40 (s, 4H), 3.21 (s, 2H), 2.50 (m, 4H).

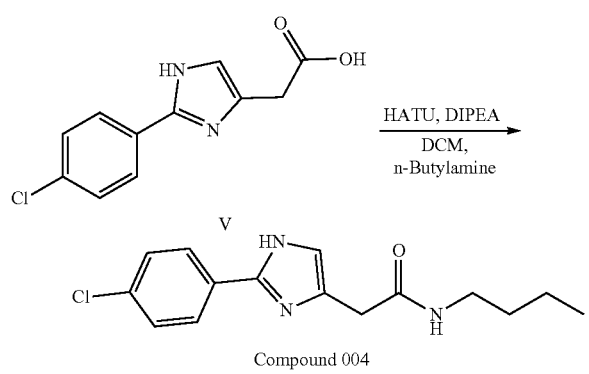

Compound 004

N-butyl-2-(2-(4-chlorophenyl)-1H-imidazol-4-yl)acetamide (Compound 004): Compound 004 (30 mg, 28%) was synthesized from compound V by following procedure C. $^1$H NMR (DMSO-d$_6$, 500 MHz): δ 12.42 (s, 1H), 7.90 (d, 3H), 7.59 (d, 2H), 6.96 (s, 1H), 3.36 (d, 2H), 3.06 (q, 2H), 1.36 (m, 2H), 1.26 (m, 2H), 0.86 (t, 3H).

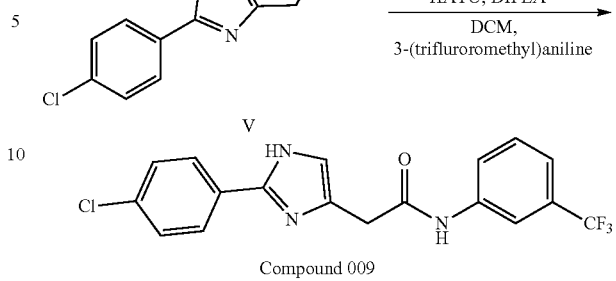

Compound 009

2-(2-(4-chlorophenyl)-1H-imidazol-4-yl)-N-(3-(trifluoromethyl)phenyl)acetamide (Compound 009): Compound 009 (110 mg, 52%) was synthesized from compound V by following procedure C. $^1$H NMR (DMSO-d$_6$, 500 MHz): δ 12.56 (s, 1H), 10.48 (s, 1H), 8.14 (s, 1H), 7.91 (m, 2H), 7.79 (d, J=8.3 Hz, 1H), 7.55 (t, J=7.9 Hz, 1H), 7.50 (d, J=8.3 Hz, 2H), 7.40 (d, J=7.6 Hz, 1H), 7.10 (s, 1H), 3.68 (s, 2H).

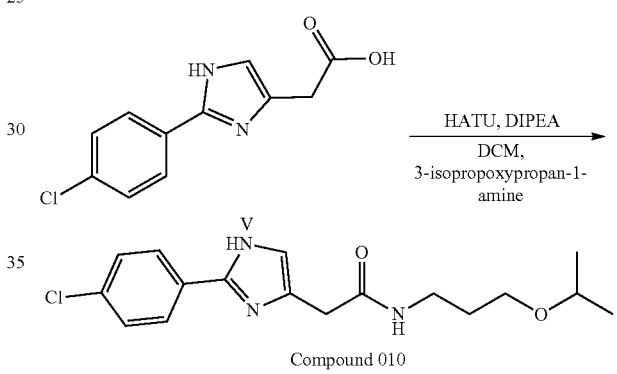

Compound 010

2-(2-(4-chlorophenyl)-1H-imidazol-4-yl)-N-(3-isopropoxypropyl)acetamide (Compound 010): Compound 010 (152 mg, 83%) was synthesized from compound V by following procedure C. $^1$H NMR (DMSO-d$_6$, 500 MHz): δ 12.90 (s, 1H), 7.90 (m, 3H), 7.52 (d, J=9.0 Hz, 2H), 7.04 (s, 1H), 3.46 (m, 1H), 3.41 (s, 2H), 3.34 (t, J=6.5 Hz, 2H), 3.12 (q, J=6.4 Hz, 2H), 1.60 (m, 2H), 1.04 (d, J=6.2 Hz, 6H).

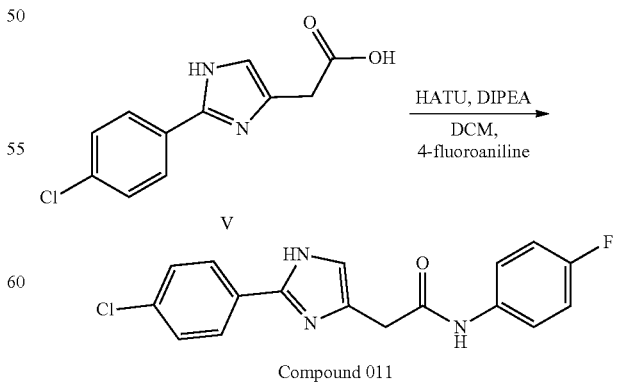

Compound 011

2-(2-(4-chlorophenyl)-1H-imidazol-4-yl)-N-(4-fluorophenyl)acetamide (compound 011): Compound 011 (60 mg, 33%) was synthesized from compound V by following procedure C. $^1$H NMR (DMSO-d$_6$, 500 MHz): δ 12.54 (s, 1H), 10.19 (s, 1H), 7.92 (d, J=8.3 Hz, 2H), 7.63 (q, J=4.8 Hz, 2H), 7.50 (d, J=9.0 Hz, 2H), 7.14 (t, J=9.0 Hz, 2H), 7.07 (s, 1H), 3.63 (s, 2H).

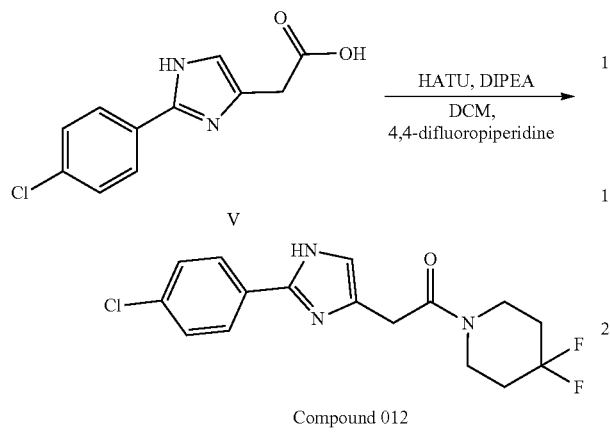

Compound 012

2-(2-(4-chlorophenyl)-1H-imidazol-4-yl)-1-(4,4-difluoropiperidin-1-yl)ethan-1-one (compound 012): Compound 012 (35 mg, 28%) was synthesized from compound V by following procedure C. $^1$H NMR (DMSO-d$_6$, 500 MHz): δ 12.52 (s, 1H), 7.90 (m, 2H), 7.50 (d, J=8.3 Hz, 2H), 7.04 (s, 1H), 3.70 (t, J=6.5 Hz, 4H), 3.59 (t, J=5.9 Hz, 2H), 1.95 (m, 4H).

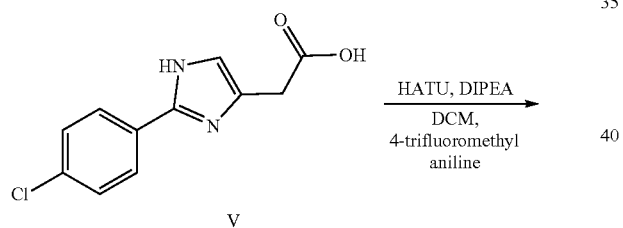

Compound 014

2-(2-(4-chlorophenyl)-1H-imidazol-4-yl)-N-(4-(trifluoromethyl)phenyl)acetamide (compound 014): Compound 014 (47 mg, 33%) was synthesized from compound V by following procedure C. $^1$H NMR (DMSO-d$_6$, 500 MHz): δ 12.50 (s, 1H), 10.50 (s, 1H), 7.92 (m, 2H), 7.83 (m, 2H), 7.68 (t, J=8.6 Hz, 2H), 7.50 (dd, J=8.6 Hz, 2.4 Hz, 2H), 7.15 (d, J=2.1 Hz, 1H), 3.65 (s, 2H).

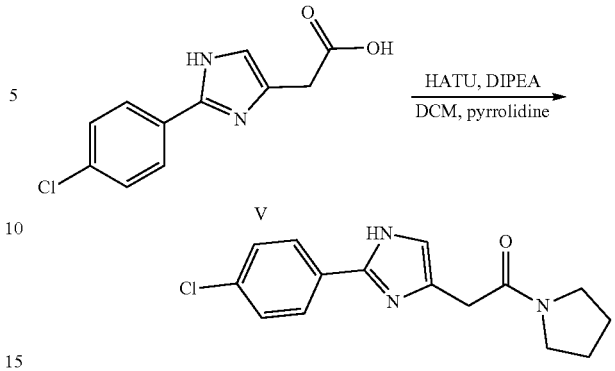

Compound 016

2-(2-(4-chlorophenyl)-1H-imidazol-4-yl)-1-(pyrrolidin-1-yl)ethan-1-one (compound 016): Compound 016 (72 mg, 45%) was synthesized from compound V by following procedure C. $^1$H NMR (DMSO-d$_6$, 500 MHz): δ 13.26 (s, 1H), 7.92 (d, J=8.3 Hz, 2H), 7.56 (d, J=7.6 Hz, 2H), 7.14 (s, 1H), 3.65 (s, 2H), 3.55 (t, J=6.9 Hz, 2H), 3.30 (m, 2H), 1.79 (q, J=6.9 Hz, 2H).

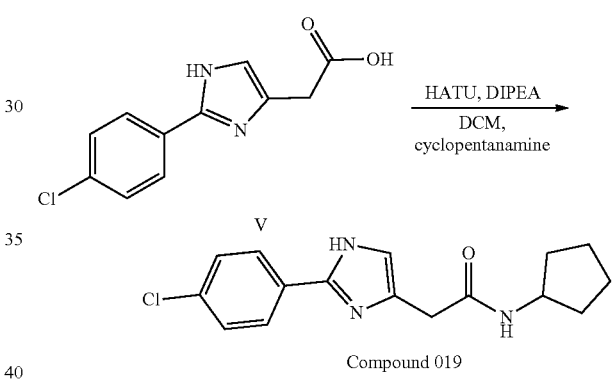

Compound 019

2-(2-(4-chlorophenyl)-1H-imidazol-4-yl)-N-cyclopentylacetamide (Compound 019): Compound 019 (76 mg, 46%) was synthesized from compound V by following procedure C. $^1$H NMR (DMSO-d$_6$, 500 MHz): δ 12.63 (s, 1H), 7.97 (d, J=7.6 Hz, 1H), 7.91 (d, J=8.3 Hz, 2H), 7.50 (d, J=9.0 Hz, 2H), 6.97 (s, 1H), 4.00 (td, J=13.8 Hz, 6.9 Hz, 1H), 3.38 (s, 2H), 1.80 (td, J=12. Hz, 6.7 Hz, 2H), 1.63 (m, 2H), 1.51 (m, 2H), 1.37 (m, 2H).

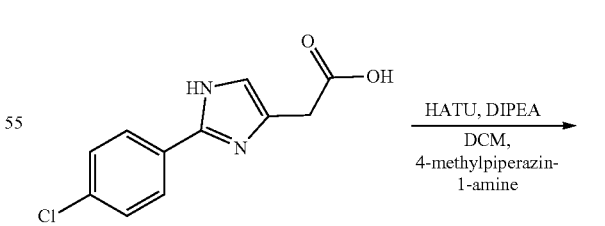

Compound 020

2-(2-(4-chlorophenyl)-1H-imidazol-4-yl)-1-(4-methylpiperazin-1-yl)ethan-1-one (compound 020): Compound 020 (63 mg, 36%) was synthesized from compound V by following procedure C.

¹H NMR (DMSO-d₆, 500 MHz): δ 12.43 (s, 1H), 7.90 (d, J=9.0 Hz, 2H), 7.49 (d, J=8.3 Hz, 2H), 7.05 (s, 1H), 3.60 (d, J=24.1 Hz, 4H), 3.46 (s, 2H), 2.27 (d, J=20.0 Hz, 4H), 2.17 (s, 3H).

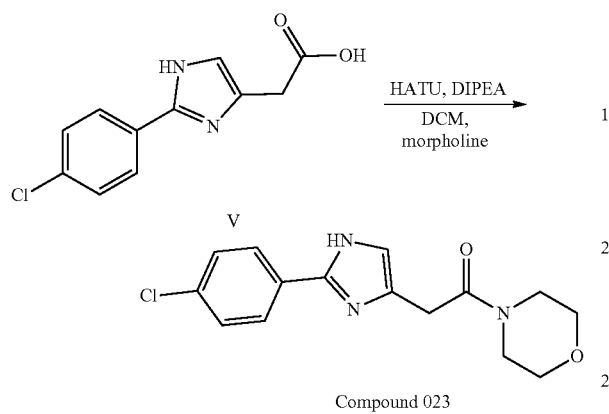

2-(2-(4-chlorophenyl)-1H-imidazol-4-yl)-1-morpholinoethan-1-one (compound 023): Compound 023 (170 mg, 76%) was synthesized from compound V by following procedure C. ¹H NMR (DMSO-d₆, 500 MHz): δ 12.44 (s, 1H), 7.90 (d, J=8.3 Hz, 2H), 7.49 (d, J=9.0 Hz, 2H), 7.07 (s, 1H), 3.75 (s, 1H), 3.61 (s, 3H), 3.55 (d, J=17.9 Hz, 5H), 3.46 (d, J=4.8 Hz, 2H).

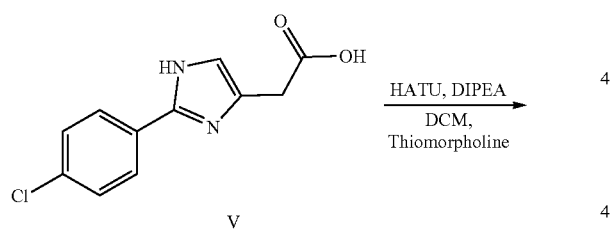

2-(2-(4-chlorophenyl)-1H-imidazol-4-yl)-1-thiomorpholinoethan-1-one (compound 024): Compound 024 (70 mg, 40%) was synthesized from compound V by following procedure C. ¹H NMR (DMSO-d₆, 500 MHz): δ 12.61 (s, 1H), 7.91 (d, J=8.3 Hz, 2H), 7.51 (d, J=8.3 Hz, 2H), 7.03 (s, 1H), 3.83 (t, J=4.8 Hz, 2H), 3.73 (t, J=4.8 Hz, 2H), 3.67 (s, 2H), 2.57 (t, J=4.8 Hz, 2H), 2.53 (t, J=4.8 Hz, 2H).

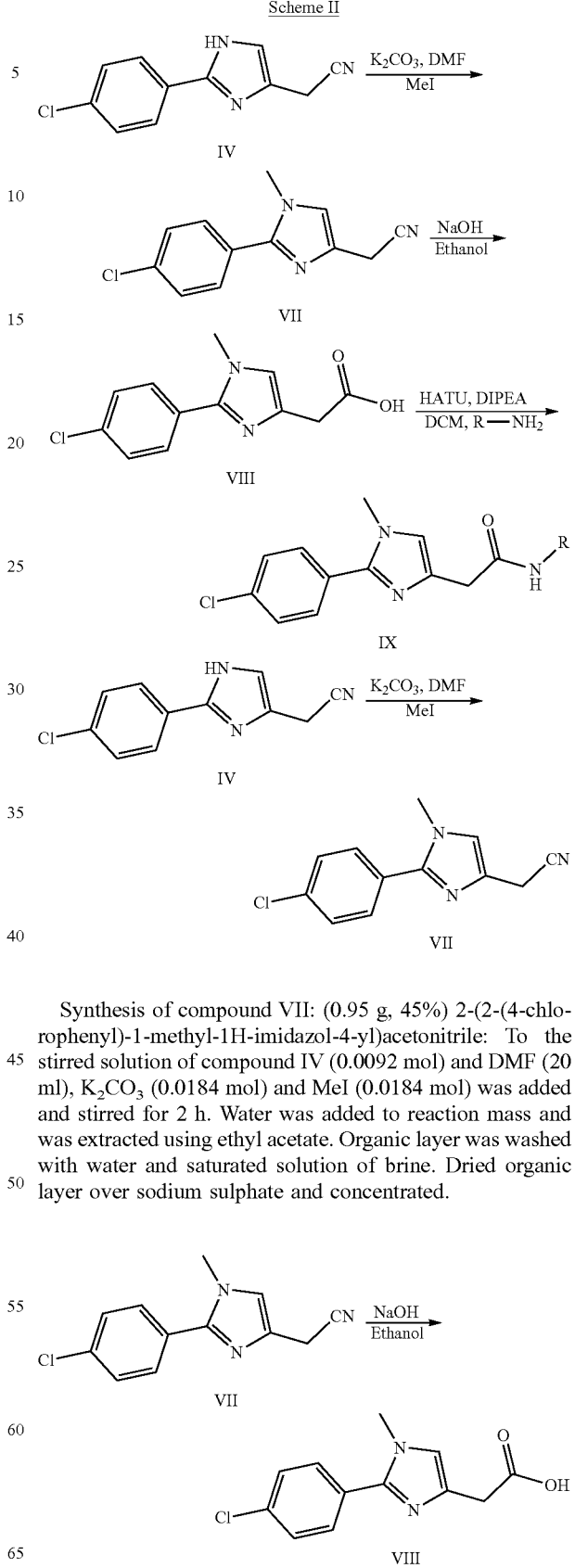

Scheme II

Synthesis of compound VII: (0.95 g, 45%) 2-(2-(4-chlorophenyl)-1-methyl-1H-imidazol-4-yl)acetonitrile: To the stirred solution of compound IV (0.0092 mol) and DMF (20 ml), K₂CO₃ (0.0184 mol) and MeI (0.0184 mol) was added and stirred for 2 h. Water was added to reaction mass and was extracted using ethyl acetate. Organic layer was washed with water and saturated solution of brine. Dried organic layer over sodium sulphate and concentrated.

Synthesis of compound VIII: 2-(2-(4-chlorophenyl)-1-methyl-1H-imidazol-4-yl)acetic acid: The compound VIII was synthesize from compound VII by following procedure B.

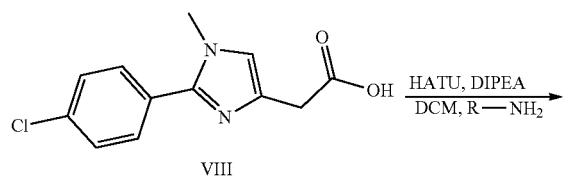

Synthesis of general compound IX: The general compound IX was synthesized from compound VIII by following procedure C.

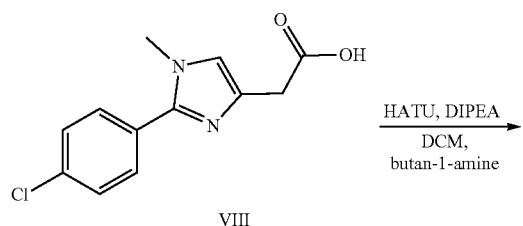

N-butyl-2-(2-(4-chlorophenyl)-1-methyl-1H-imidazol-4-yl)acetamide (compound 005): Compound 005 (35 mg, 33%) was synthesized from compound VIII by following procedure C. ¹H NMR (DMSO-d₆, 500 MHz): δ 7.91 (s, 1H), 7.70 (d, 2H), 7.55 (d, 2H), 7.12 (s, 1H), 3.72 (s, 3H), 3.32 (d, 2H), 3.04 (d, 2H), 1.36 (m, 2H), 1.26 (m, 2H), 0.86 (t, 3H).

2-(2-(4-chlorophenyl)-1-methyl-1H-imidazol-4-yl)-N-(2-morpholinoethyl)acetamide (compound 006): Compound 006 (44 mg, 35%) was synthesized from compound VIII by following procedure C. ¹H NMR (DMSO-d₆, 500 MHz): δ 7.57 (d, 2H), 7.44 (d, 3H), 6.87 (s, 1H), 3.71 (s, 3H), 3.56 (m, 6H), 3.40 (d, 2H), 2.53 (s, 3H), 2.48 (s, 3H).

2-(2-(4-chloro phenyl)-1-methyl-1H-imidazol-4-yl)-N-(3(trifluoromethyl)phenyl)acetamide (compound 007): Compound 007 (85 mg, 62%) was synthesized from compound VIII by following procedure C. ¹H NMR (DMSO-d₆, 500 MHz): δ 10.47 (s, 1H), 8.14 (s, 1H), 7.78 (d, 1H), 7.70 (d, 2H), 7.54 (q, 3H), 7.39 (d, 1H), 7.17 (s, 1H), 3.73 (s, 3H), 3.60 (s, 2H).

2-(2-(4-chloro phenyl)-1-methyl-1H-imidazol-4-yl)-N-(3-isopropoxypropyl)acetamide (compound 008): Compound 008 (95 mg, 78%) was synthesized from compound VIII by following procedure C. ¹H NMR (DMSO-d₆, 500 MHz): δ 7.88 (t, J=5.3 Hz, 1H), 7.71 (d, J=9.0, 2H), 7.54 (d, J=2H), 7.12 (s, 1H), 3.72 (s, 3H), 3.45 (m, 2H), 3.34 (t, J=6.5 Hz, 3H), 3.10 (q, J=6.7 Hz, 2H), 1.59 (m, 2H), 1.03 (d, J=6.2 Hz, 6H).

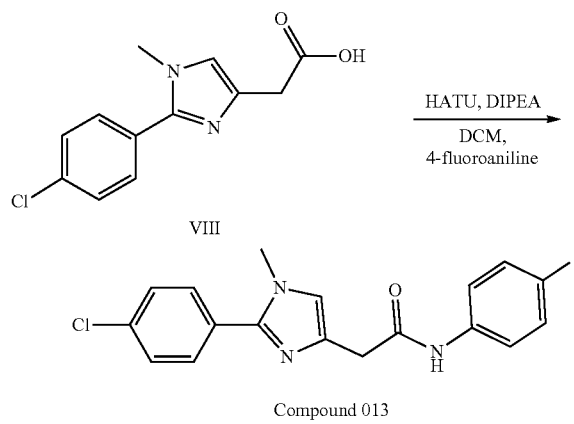

Compound 013

2-(2-(4-chloro phenyl)-1-methyl-1H-imidazol-4-yl)-N-(4-fluorophenyl)acetamide (compound 013): Compound 013 (60 mg, 31%) was synthesized from compound VIII by following procedure C. $^1$H NMR (DMSO-d$_6$, 500 MHz): δ 10.16 (s, 1H), 7.70 (m, 2H), 7.62 (m, 2H), 7.53 (m, 2H), 7.13 (m, 3H), 3.72 (s, 3H), 3.55 (s, 2H).

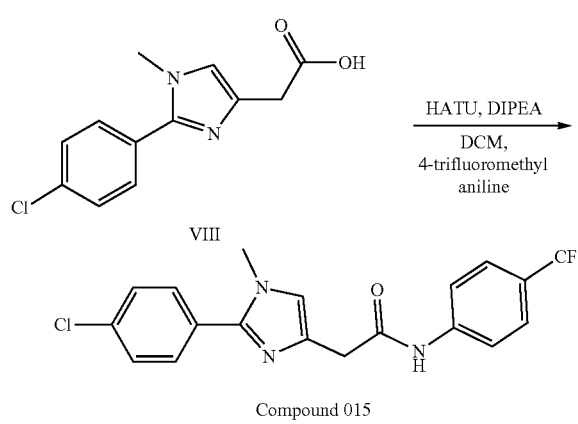

Compound 015

2-(2-(4-chlorophenyl)-1-methyl-1H-imidazol-4-yl)-N-(4-(trifluoromethyl)phenyl)acetamide (compound 015): Compound 015 (47 mg, 33%) was synthesized from compound VIII by following procedure C. $^1$H NMR (DMSO-d$_6$, 500 MHz): δ 10.50 (s, 1H), 7.82 (d, J=8.3 Hz, 2H), 7.70 (d, J=9.0 Hz, 2H), 7.67 (d, J=9.0 Hz, 2H), 7.52 (d, J=9.0 Hz, 2H), 3.73 (s, 3H), 3.61 (s, 2H).

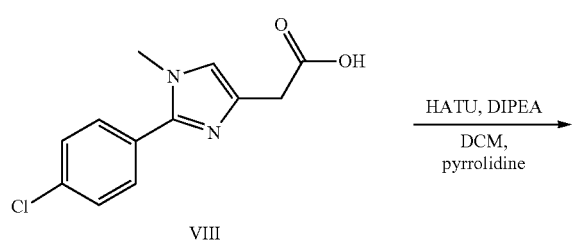

VIII

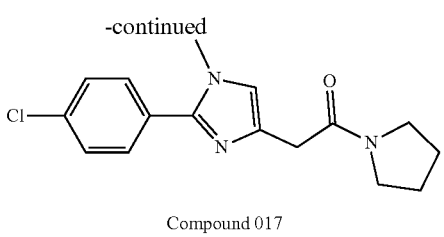

Compound 017

2-(2-(4-chlorophenyl)-1-methyl-1H-imidazol-4-yl)-1-(pyrrolidin-1-yl)ethan-1-one (compound 017): Compound 017 (67 mg, 40%) was synthesized from compound VIII by following procedure C. $^1$H NMR (DMSO-d$_6$, 500 MHz): δ 7.70 (d, J=8.3 Hz, 2H), 7.53 (d, J=9.0 Hz, 2H), 7.11 (s, 1H), 3.72 (s, 3H), 3.56 (m, 2H), 3.51 (s, 2H), 3.28 (t, J=6.9 Hz, 2H), 1.87 (m, 2H), 1.77 (m, 2H).

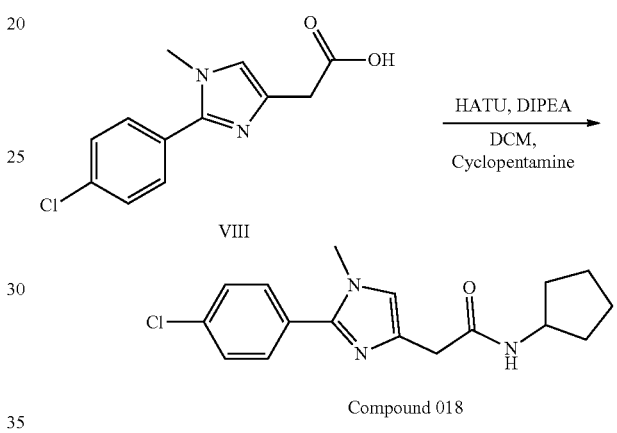

Compound 018

2-(2-(4-chloro phenyl)-1-methyl-1H-imidazol-4-yl)-N-cyclopentylacetamide (compound 018):

Compound 018 (111 mg, 64%) was synthesized from compound VIII by following procedure C. $^1$H NMR (DMSO-d$_6$, 500 MHz): δ 7.94 (d, J=7.6 Hz, 1H), 7.69 (dd, J=6.9 Hz, 2.1 Hz, 2H), 7.52 (m, 2H), 7.04 (s, 1H), 3.98 (td, J=13.4 Hz, 6.9 Hz, 1H), 3.71 (s, 3H), 3.29 (s, 2H), 1.79 (td, J=12.1 Hz, 6.9 Hz, 2H), 1.62 (m, 2H), 1.49 (m, 2H), 1.37 (m, 2H).

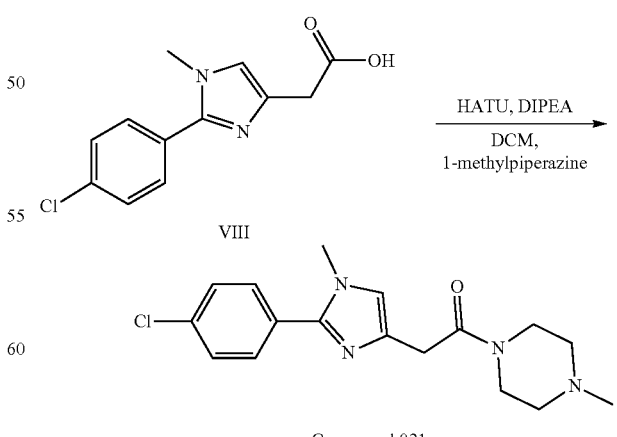

Compound 021

2-(2-(4-chlorophenyl)-1-methyl-1H-imidazol-4-yl)-1-(4-methylpiperazin-1-yl)ethan-1-one (compound 021): Compound 021 (59 mg, 32%) was synthesized from compound VIII by following procedure C. ¹H NMR (DMSO-d₆, 500 MHz): δ 7.70 (m, 2H), 7.53 (dd, J=6.9 Hz, 2.1 Hz, 2H), 7.07 (s, 1H), 3.72 (s, 3H), 3.56 (d, J=6.9 Hz, 4H), 3.45 (t, J=4.5 Hz, 2H), 2.25 (dt, J=18.6 Hz, 5.2 Hz, 4H), 2.16 (s, 3H).

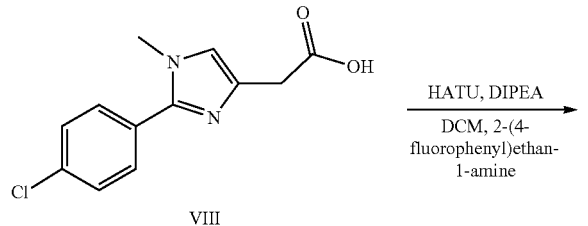

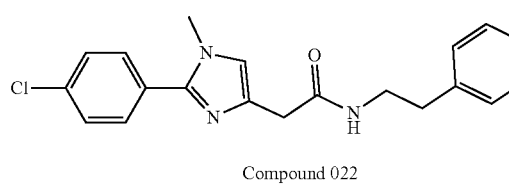

Compound 022

2-(2-(4-chlorophenyl)-1-methyl-1H-imidazol-4-yl)-N-(4-fluorophenethyl)acetamide (compound 022): Compound 022 (180 mg, 88%) was synthesized from compound VIII by following procedure C. ¹H NMR (DMSO-d₆, 500 MHz): δ 7.97 (s, 1H), 7.69 (d, J=8.3 Hz, 2H), 7.55 (d, J=8.3 Hz, 2H), 7.22 (dd, J=8.3 Hz, 5.5 Hz, 2H), 7.06 (m, 2H), 3.72 (s, 3H), 3.56 (s, 2H), 3.28 (q, J=6.7 Hz, 2H), 2.70 (t, J=7.2 Hz, 2H).

Scheme III

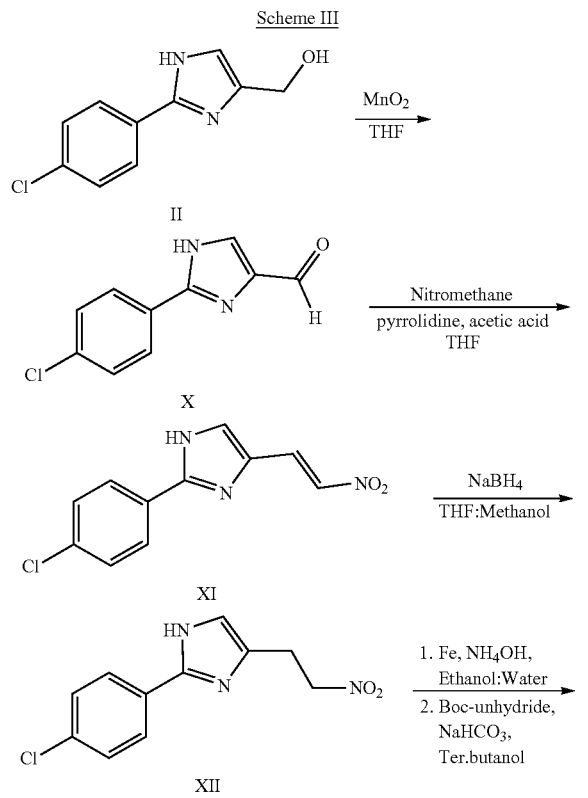

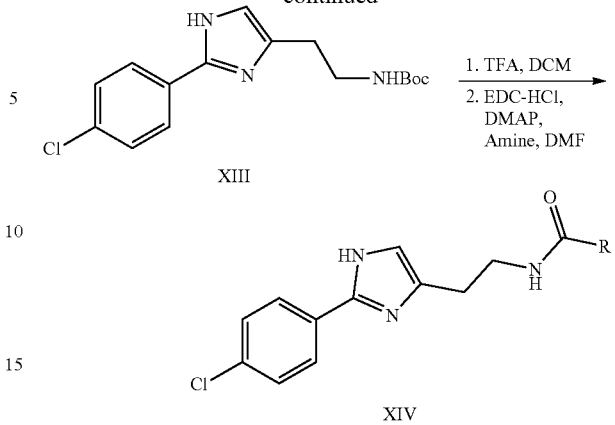

Procedure D:

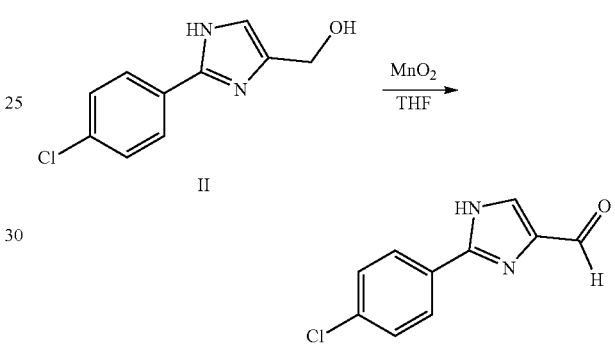

Synthesis of Compound X: (84%, 7.5 g) 2-(4-chlorophenyl)-1H-imidazole-4-carbaldehyde: To the stirred solution of compound II (0.043 mol) and THF (100 ml), MnO2 (0.65 mol) was added slowly, stirred for 3 Hours at RT, filtered reaction mass through celite bed, washed celite bed with 10% MeOH in DCM (60 ml), concentrated ml and dried well.

Procedure D:

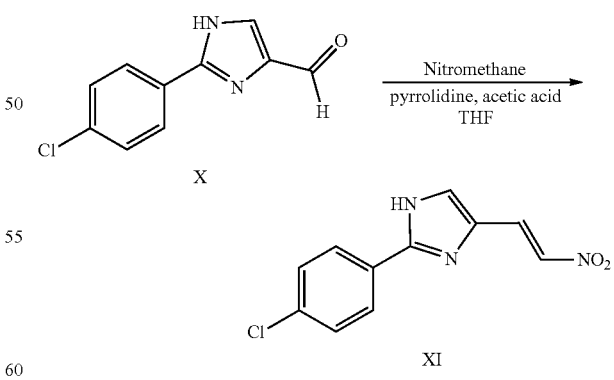

Synthesis of Compound XI: (3 g, 93%) (E)-2-(4-chlorophenyl)-4-(2-nitrovinyl)-1H-imidazole: To the stirred solution of compound X (0.013 mol) and THF (50 ml), Nitromethane (0.026 mol), pyrrolidine (0.0013 mol) and acetic acid (0.0013 mol) was added at RT. Stirred reaction mass for 3 hours, concentrate reaction mass at low temperature (35° C.) up to 90%, water was added to the concentrated mass, solid was filter through Buckner funnel, solid was washed with ethyl acetate (30 ml), filtered and dried well. $^1$H NMR (DMSO-$d_6$, 500 MHz): δ 13.27 (s, 1H), 8.04 (m, 4H), 7.84 (s, 1H), 7.59 (d, J=8.4 Hz, 2H).

Procedure F:

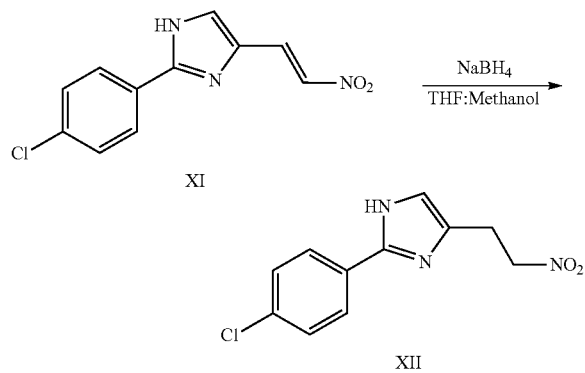

Synthesis of Compound XII: (0.45 mg, 44%) 2-(4-chlorophenyl)-4-(2-nitroethyl)-1H-imidazole:

To the stirred solution of compound XI (0.0016 mol) in THF: Methanol (10:1 ml), sodium borohydride (0.0018 mol) was added slowly at cooled condition, Stirred reaction mass for half hour. 1 N HCl was added slowly at cold condition (12 ml), ethyl acetate was added, organic layer was washed with water and saturated brine solution. Dried organic layer over sodium sulphate and concentrated under reduced pressure and purified by column chromatography. $^1$H NMR (DMSO-$d_6$, 500 MHz): δ 11.61 (s, 1H), 7.83 (m, 2H), 7.36 (dd, J=6.9 Hz, 2.1 Hz, 2H), 6.88 (s, 1H), 4.73 (t, J=7.2 Hz, 2H), 3.32 (t, J=7.2 Hz, 2H).

Procedure G:

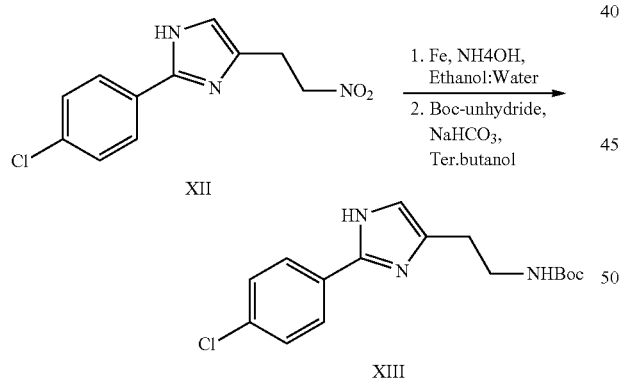

Synthesis of Compound XIII: (1.2 g, 48%) tert-butyl (2-(2-(4-chlorophenyl)-1H-imidazol-4-yl)ethyl)carbamate:

To the stirred solution of compound XII (0.0048 mol) and Ethanol: water (24 ml: 8 ml). NH$_4$Cl (0.048 mol) followed Fe (0.048 mol) was added at RT, refluxed for 3 hours. Reaction mass was cooled to RT, passed through celite bed and celite bed was washed with ethyl acetate (15 ml) and water (10 ml), concentrated ethyl acetate. To the stirred solution of above concentrated mass and ter. butanol (20 ml), NaHCO$_3$ (0.019 mol) and Boc anhydride (Di-tert-butyl dicarbonate) (0.019 mol) was added. Stirred reaction mass for overnight, concentrate reaction mass, ethyl acetate (30 ml) was added, organic layer was washed with water and saturated brine solution, concentrate and crude was washed with diethyl-ether (20 ml) two times.

$^1$H NMR (DMSO-$d_6$, 500 MHz): δ 12.33 (s, 1H), 7.89 (d, J=8.4 Hz, 2H), 7.48 (d, J=8.0 Hz, 2H), 6.88 (m, 1H), 6.14 (s, 1H), 3.19 (q, J=6.7 Hz, 2H), 2.67 (dt, J=36. Hz, 7.4 Hz, 2H), 1.37 (m, 9H).

Procedure H:

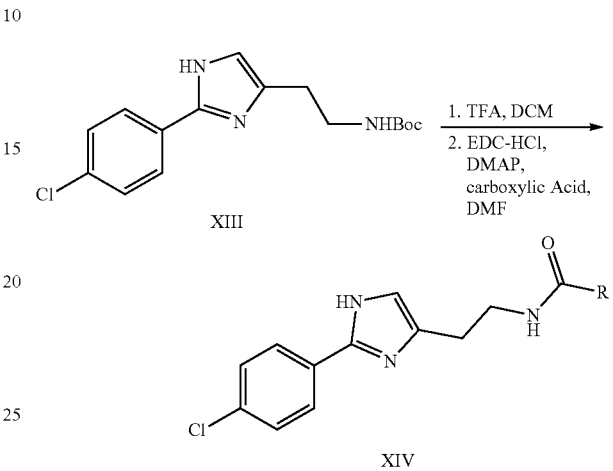

Synthesis of compound XIV: To the stirred solution of compound XIII (0.43 mmol) and DCM (10 ml), TFA (2 ml) was added at 0° C. stirred for 2 hours, concentrated reaction mass and was washed with diethyl-ether (5 ml). To the above stirred solution with DMF (8 ml), EDC-HCl (0.47 mmol), DMAP (1.43 mmol) and Acid (0.47 mmol) were added. Stirred this reaction mass for overnight, Ethyl acetate was added, washed with saturated NaHCO$_3$, water and saturated brine solution, organic layer was dried over sodium sulphate, concentrated and purified by column chromatography.

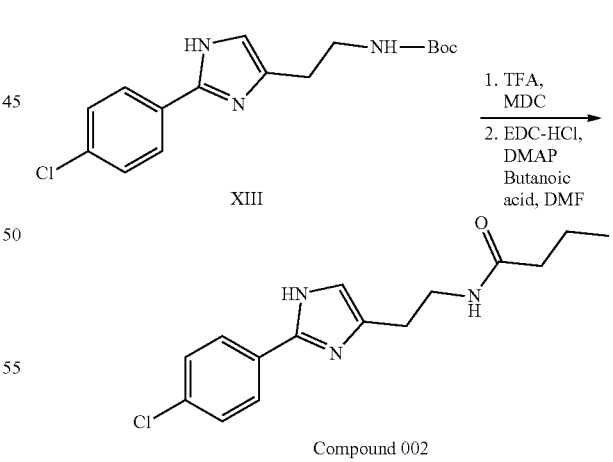

Compound 002

N-(2-(2-(4-chlorophenyl)-1H-imidazol-4-yl)ethyl)butyramide (compound 002): Compound 002 (18 mg, 51%) was synthesized from compound XIII by following procedure H. $^1$H NMR (DMSO-$d_6$, 500 MHz): δ 12.35 (s, 1H), 7.89 (m, 3H), 7.49 (dt, J=9.1 Hz, 2.3 Hz, 2H), 6.92 (s, 1H), 3.31 (m, 2H), 2.67 (t, J=7.1 Hz, 2H), 2.03 (t, J=7.4 Hz, 2H), 1.50 (td, J=14.1 Hz, 7.4 Hz, 2H), 0.84 (t, J=7.4 Hz, 3H).

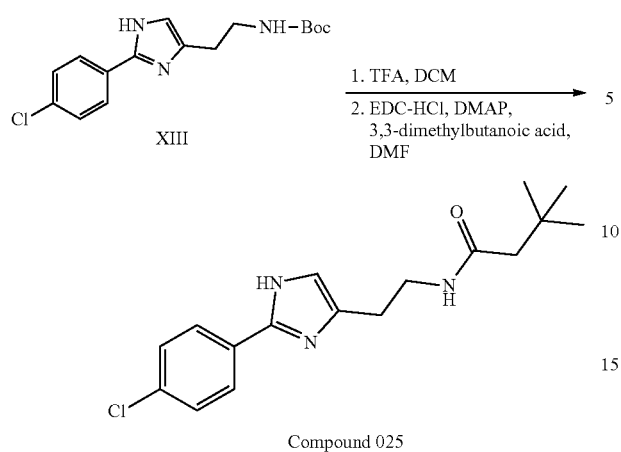

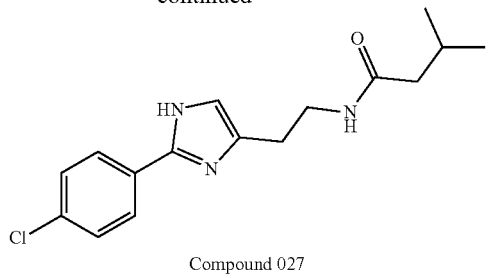

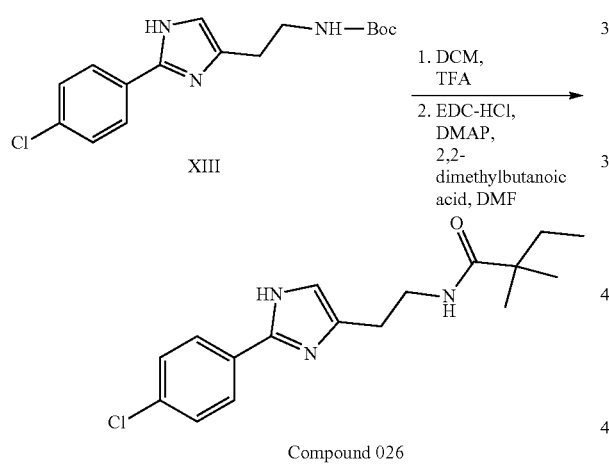

N-(2-(2-(4-chlorophenyl)-1H-imidazol-4-yl)ethyl)-3,3-dimethylbutanamide (compound 025): Compound 025 (77 mg, 54%) was synthesized from compound XIII by following procedure H. $^1$H NMR (DMSO-$d_6$, 500 MHz): δ 12.80 (s, 1H), 7.91 (m, 2H), 7.84 (t, J=5.5 Hz, 1H), 7.56 (d, J=9.0 Hz, 2H), 7.10 (s, 1H), 3.35 (d, d, J=6.9 Hz, 2H), 2.71 (t, J=7.2 Hz, 2H), 1.94 (s, 2H), 0.93 (s, 9H).

N-(2-(2-(4-chlorophenyl)-1H-imidazol-4-yl)ethyl)-2,2-dimethylbutanamide (compound 026): Compound 026 (75 mg, 35%) was synthesized from compound XIII by following procedure H. $^1$H NMR (DMSO-$d_6$, 500 MHz): δ 12.33 (d, 1H), 7.90 (d, J=8.3 Hz, 2H), 7.56 (m, 1H), 7.49 (d, J=9.0 Hz, 2H), 7.00 (s, 1H), 3.36 (t, 2H), 2.74 (t, J=6.9 Hz, 1H), 2.65 (m, 1H), 1.45 (q, J=7.3 Hz, 2H), 1.03 (d, J=9.6 Hz, 6H), 0.71 (q, J=8.0 Hz, 3H).

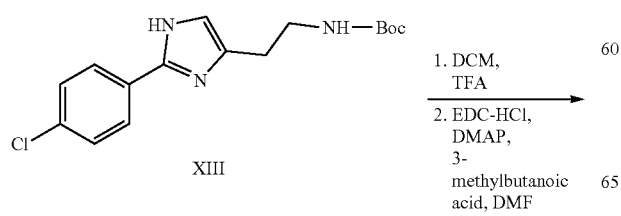

N-(2-(2-(4-chlorophenyl)-1H-imidazol-4-yl)ethyl)-3-methylbutanamide (compound 027): Compound 027 (58 mg, 28%) was synthesized from compound XIII by following procedure H. $^1$H NMR (DMSO-$d_6$, 500 MHz): δ 12.52 (s, 1H), 7.90 (m, 2H), 7.87 (t, J=6.2 Hz, 1H), 7.50 (d, J=9.0 Hz, 2H), 6.94 (s, 1H), 3.55 (t, 2H), 2.67 (t, J=7.2 Hz, 2H), 1.97 (td, J=6.2 Hz, 2.8 Hz, 1H), 1.93 (s, 2H), 0.85 (J=6.2 Hz, 6H).

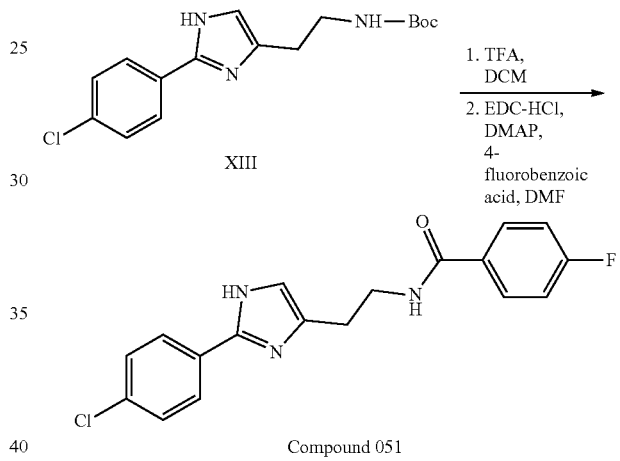

N-(2-(2-(4-chlorophenyl)-1H-imidazol-4-yl)ethyl)-4-fluorobenzamide (compound 051): Compound 051 (45 mg, 28%) was synthesized from compound XIII by following procedure H. $^1$H NMR (DMSO-$d_6$, 500 MHz): δ 12.37 (s, 1H), 8.62 (t, J=5.5 Hz, 1H), 7.91 (m, 4H), 7.50 (m, 2H), 7.30 (m, 2H), 3.53 (m, 2H), 2.81 (d, J=21.3 Hz, 3.4 Hz, 2H).

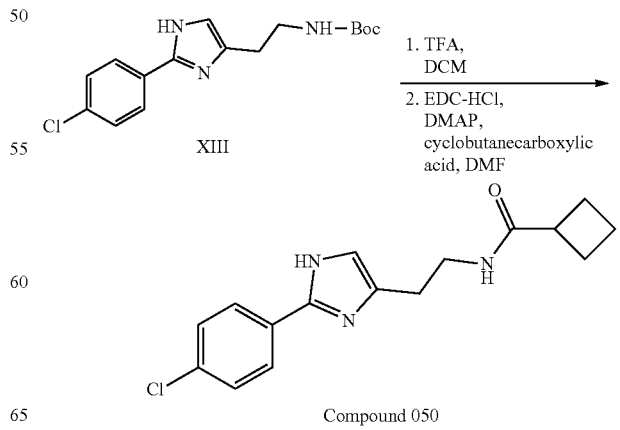

N-(2-(2-(4-chlorophenyl)-1H-imidazol-4-yl)ethyl)cyclobutanecarboxamide (compound 050): Compound 050 (60 mg, 42%) was synthesized from compound XIII by following procedure H. $^1$H NMR (DMSO-d$_6$, 500 MHz): δ 12.36 (s, 1H), 7.89 (m, 2H), 7.73 (t, J=5.4 Hz, 1H), 7.49 (m, 2H), 6.91 (s, 1H), 3.30 (dd, J=13.4 Hz, 7.4 Hz, 2H), 2.97 (m, 1H), 2.67 (t, J=7.2 Hz, 2H), 1.99 (m, 2H), 1.86 (m, 1H), 1.74 (m, 1H)

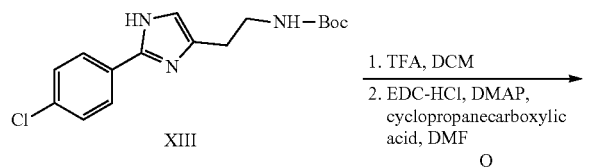

Compound 046

N-(2-(2-(4-chlorophenyl)-1H-imidazol-4-yl)ethyl)cyclopropanecarboxamide (compound 046):

Compound 046 (95 mg, 70%) was synthesized from compound XIII by following procedure H. $^1$H NMR (DMSO-d$_6$, 500 MHz): δ 12.34 (s, 1H), 8.12 (s, 1H), 7.90 (d, J=8.4 Hz, 2H), 7.49 (d, J=8.4 Hz, 2H), 7.01 (s, 1H), 3.36 (d, J=7.3 Hz, 2H), 2.69 (d, J=31.3 Hz, 2H), 1.53 (m, 1H), 0.64 (m, 4H).

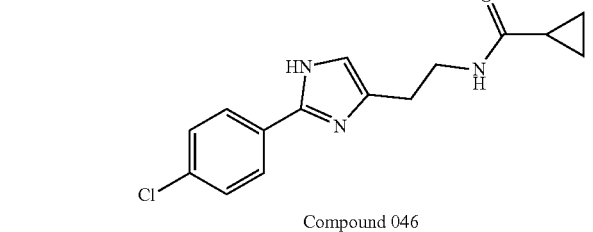

Compound 055

N-(2-(2-(4-chlorophenyl)-1H-imidazol-4-yl)ethyl)cyclopent-1-ene-1-carboxamide (compound 055): Compound 055 (52 mg, 35%) was synthesized from compound XIII by following procedure H. $^1$H NMR (DMSO-d$_6$, 500 MHz): δ 12.38 (s, 1H), 7.92 (m, 3H), 7.49 (dd, J=6.9 Hz, 1.8 Hz, 2H), 6.94 (s, 1H), 6.45 (m, 1H), 3.39 (m, 2H), 2.71 (m, 2H), 2.43 (m, 4H), 1.86 (m, 2H).

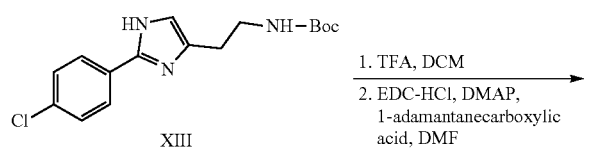

Compound 064

(3r,5r,7r)-N-(2-(2-(4-chlorophenyl)-1H-imidazol-4-yl)ethyl)adamantane-1-carboxamide (compound 064): Compound 064 (61 mg, 33%) was synthesized from compound XIII by following procedure H. $^1$H NMR (DMSO-d$_6$, 500 MHz): δ 12.35 (d, J=20.7, 1H), 7.90 (m, 2H), 7.60 (t, J=5.2 Hz, 1H), 7.49 (dd, J=6.7 Hz, 1.9 Hz, 2H), 7.01 (s, 1H), 2.73 (m, 1H), 2.63 (t, J=7.3 Hz, 1H), 1.96 (s, 3H), 1.75 (m, 6H), 1.65 (dd, J=20.7 Hz, 12.4 Hz, 6H).

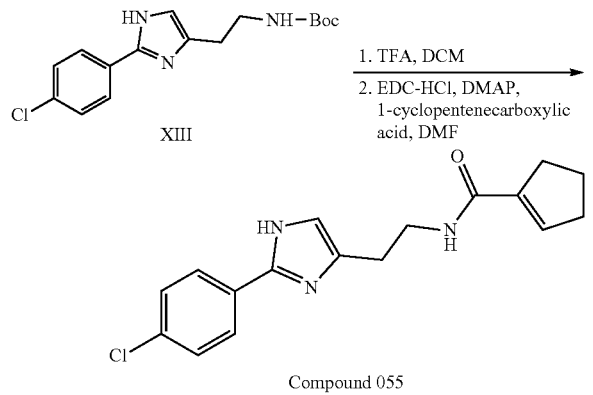

Compound 053

N-(2-(2-(4-chlorophenyl)-1H-imidazol-4-yl)ethyl)-4-(trifluoromethyl)benzamide (Compound 053): Compound 053 (61 mg, 33%) was synthesized from compound XIII by following procedure H. $^1$H NMR (DMSO-d$_6$, 500 MHz): δ 12.54 (s, 1H), 8.84 (t, J=5.5 Hz, 1H), 8.04 (d, J=8.1 Hz, 2H), 7.88 (m, 4H), 7.50 (dd, J=6.8 Hz, 1.9 Hz, 2H), 7.00 (s, 1H), 3.57 (dd, J=13.1 Hz, 7.1 Hz, 2H), 2.85 (m, 2H).

Compound 054

N-(2-(2-(4-chlorophenyl)-1H-imidazol-4-yl)ethyl)-3,5-difluorobenzamide (compound 054): Compound 054 (76 mg, 38%) was synthesized from compound XIII by following procedure H. ¹H NMR (DMSO-d₆, 500 MHz): δ 12.44 (s, 1H), 8.78 (t, J=5.5 Hz, 1H), 7.90 (d, J=8.5 Hz, 2H), 7.54 (m, 2H), 7.48 (m, 3H), 7.00 (s, 1H), 3.54 (dd, J=13.1 Hz, 7.1 Hz, 2H), 2.81 (s, 2H).

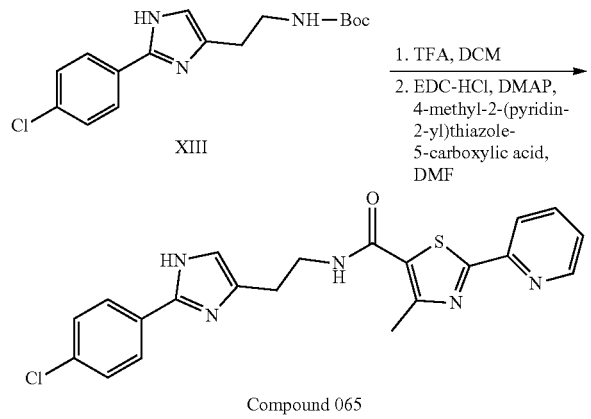

Compound 065

N-(2-(2-(4-chlorophenyl)-1H-imidazol-4-yl)ethyl)-4-methyl-2-(pyridin-2-yl)thiazole-5-carb oxamide (compound 065): Compound 065 (75 mg, 38%) was synthesized from compound XIII by following procedure H. ¹H NMR (DMSO-d₆, 500 MHz): δ 12.41 (s, 1H), 8.65 (d, J=4.3 Hz, 1H), 8.47 (t, J=5.3 Hz, 1H), 8.12 (d, J=7.8 Hz, 1H), 7.98 (td, J=7.7 Hz, 1.5 Hz, 1H), 7.92 (t, J=8.5 Hz, 2H) 7.52 (m, 2H), 7.09 (s, 1H), 3.51 (d, J=5.6 Hz, 2H), 2.83 (m, 2H), 2.61 (m, 2H).

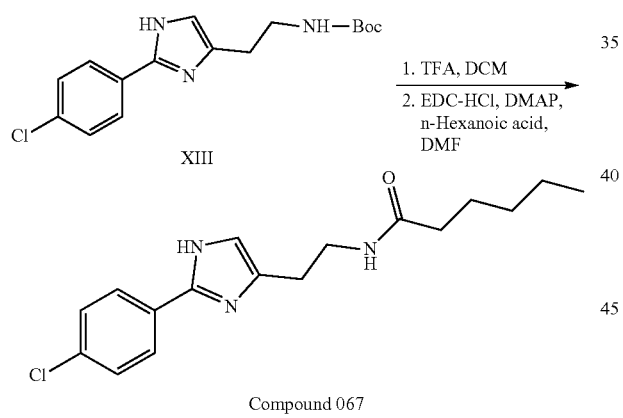

Compound 067

N-(2-(2-(4-chlorophenyl)-1H-imidazol-4-yl)ethyl) hexanamide (compound 067): Compound 067 (75 mg, 50%) was synthesized from compound XIII by following procedure H. ¹H NMR (DMSO-d₆, 500 MHz): δ 12.33 (s, 1H), 7.89 (d, J=9.0 Hz, 2H), 7.83 (s, 1H), 7.48 (d, J=9.0 Hz, 2H), 7.00 (s, 1H), 3.3 (t, 2H), 2.67 (m, 2H), 2.04 (t, J=7.2 Hz, 2H), 1.48 (m, 2H), 1.22 (qd, J=14.1 Hz, 7.1 Hz, 4H), 0.84 (t, J=6.9 Hz, 3H).

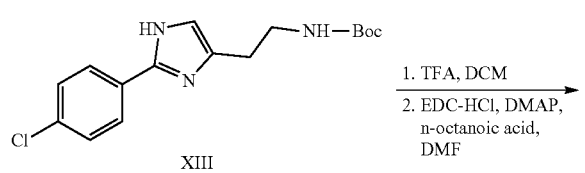

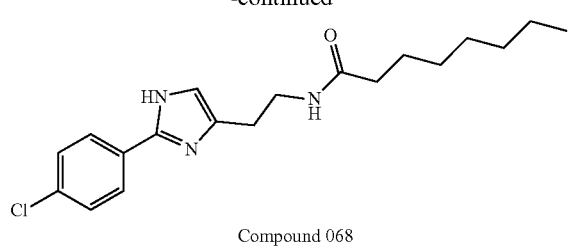

Compound 068

N-(2-(2-(4-chlorophenyl)-1H-imidazol-4-yl)ethyl)octanamide (compound 068): Compound 068 (70 mg, 43%) was synthesized from compound XIII by following procedure H. ¹H NMR (DMSO-d₆, 500 MHz): δ 12.32 (d, J=8.3 Hz, 1H), 7.90 (dd, J=9.0 Hz, 2.8 Hz, 2H), 7.83 (t, J=5.5 Hz, 1H), 7.48 (m, 2H), 7.00 (s, 1H), 3.30 (t, J=6.9 Hz, 2H), 2.72 (t, J=6.9 Hz, 1H), 2.63 (t, J=7.6 Hz, 1H), 2.04 (t, J=7.2 Hz, 2H), 1.48 (d, J=6.9 Hz, 2H), 1.23 (m, 9H), 0.84 (t, J=3H).

Scheme IV

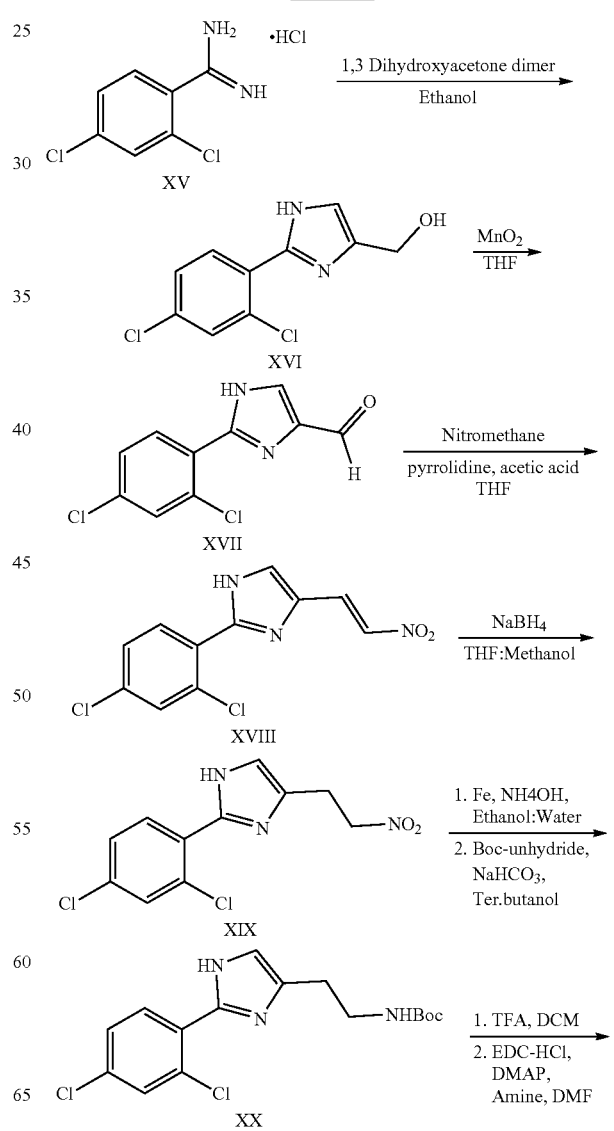

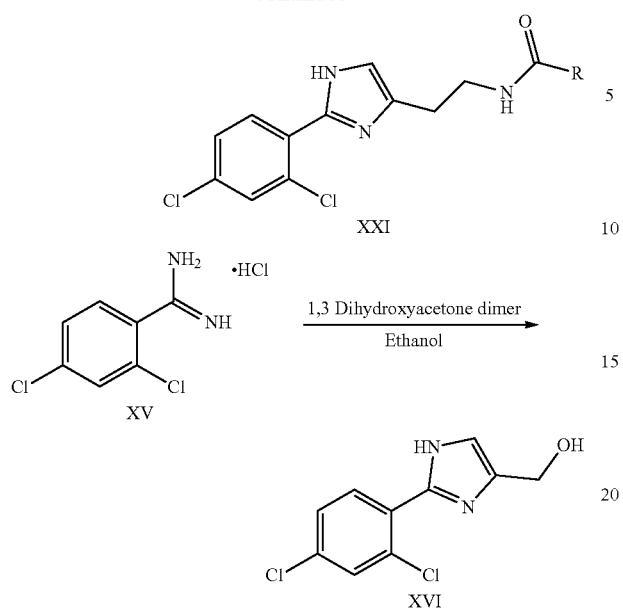

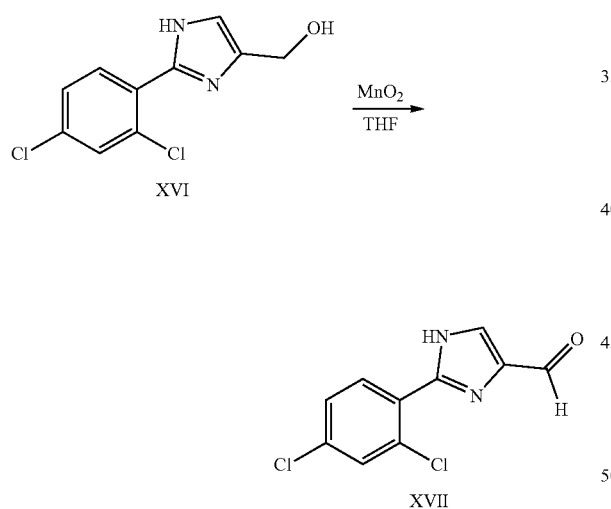

Synthesis of Compound XVI (51%): (2-(2,4-dichlorophenyl)-1H-imidazol-4-yl)methanol: The compound XVI was synthesized from 2,4 dichlorobenzamidine hydrochloride by following procedure A.

Synthesis of Compound XVII (80%):2-(2,4-dichlorophenyl)-1H-imidazole-4-carbaldehyde: The compound XVII was synthesized from compound XVI by following procedure D.

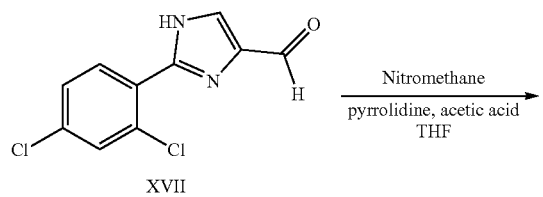

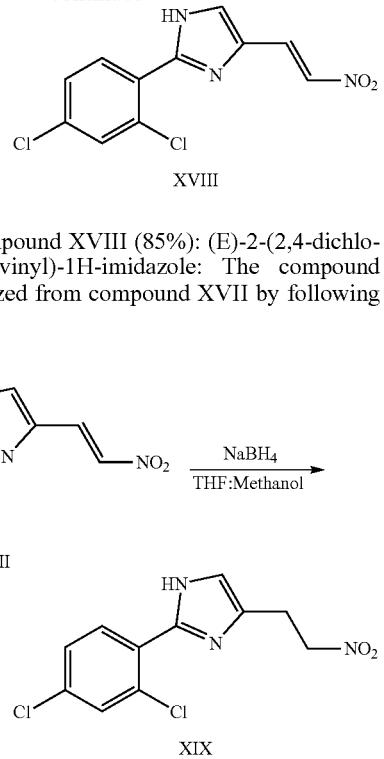

Synthesis of Compound XVIII (85%): (E)-2-(2,4-dichlorophenyl)-4-(2-nitrovinyl)-1H-imidazole: The compound XVIII was synthesized from compound XVII by following procedure E.

Synthesis of Compound XIX (35%): 2-(2,4-dichlorophenyl)-4-(2-nitroethyl)-1H-imidazole: The compound XIX was synthesized from compound XVIII by following procedure F.

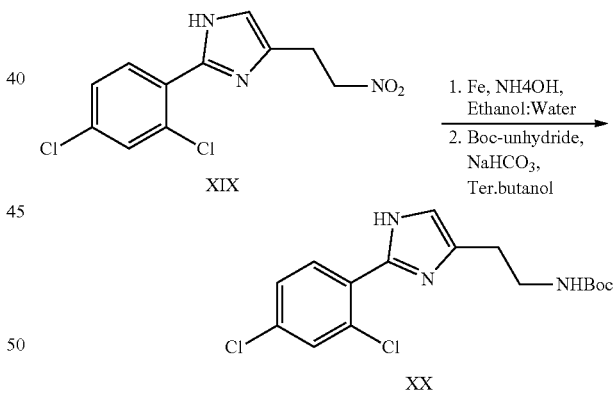

Synthesis of Compound XX (40%): s tert-butyl (2-(2-(2,4-dichlorophenyl)-1H-imidazol-4-yl)ethyl)carbamate: The compound XX was synthesized from compound XIX by following procedure G.

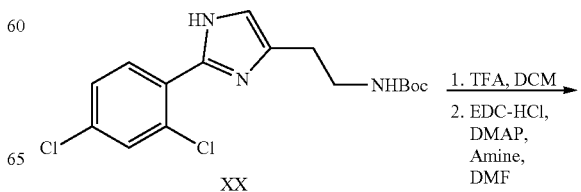

-continued

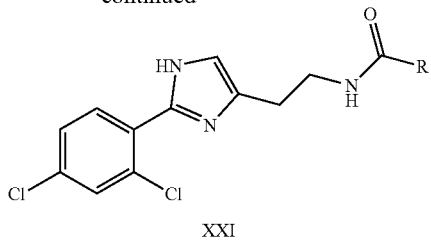

XXI

Synthesis of general compound XXI: The compound XXI was synthesized from compound XX by following procedure H.

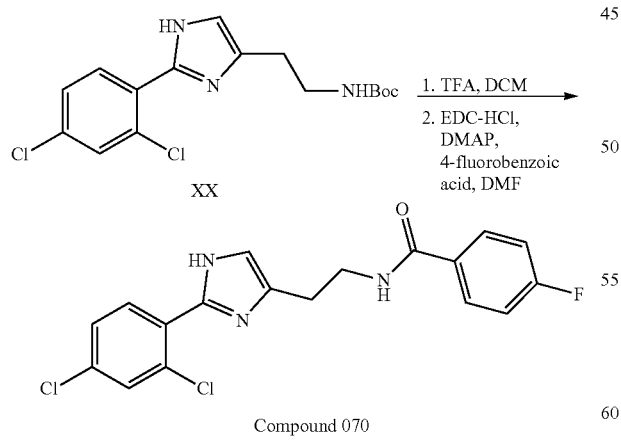

Compound 066

N-(2-(2-(2,4-dichlorophenyl)-1H-imidazol-4-yl)ethyl)-4-(trifluoromethyl)benzamide: (compound 066): Compound 066 (52 mg, 29%) was synthesized from compound XX by following procedure H. ¹H NMR (DMSO-d$_6$, 500 MHz): δ 12.16 (d, 1H), 8.84 (s, 1H), 8.04 (d, J=8.3 Hz, 2H), 7.84 (m, 3H), 7.74 (m, 1H), 7.50 (dd, J=8.3 Hz, 2.1 Hz, 1H), 7.10 (s, 1H), 3.75 (q, J=6.9 Hz, 2H), 2.91 (q, J=6.2 Hz, 1H), 2.82 (t, J=7.2 Hz, 1H).

Compound 070

N-(2-(2-(2,4-dichlorophenyl)-1H-imidazol-4-yl)ethyl)-4-fluorobenzamide (compound 070):

Compound 070 (50 mg, 31%) was synthesized from compound XX by following procedure H. ¹H NMR (DMSO-d$_6$, 500 MHz): δ 12.14 (s, 1H), 8.63 (t, J=5.2 Hz, 1H), 7.91 (m, 2H), 7.81 (s, 1H), 7.71 (d, J=2.1 Hz, 1H), 7.51 (dd, J=8.3 Hz, 2.1 Hz, 1H), 7.30 (m, 2H), 7.07 (s, 1H), 3.54 (q, J=6.7 Hz, 2H), 2.86 (d, J=31.0 Hz, 2H).

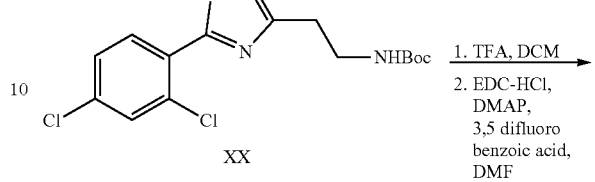

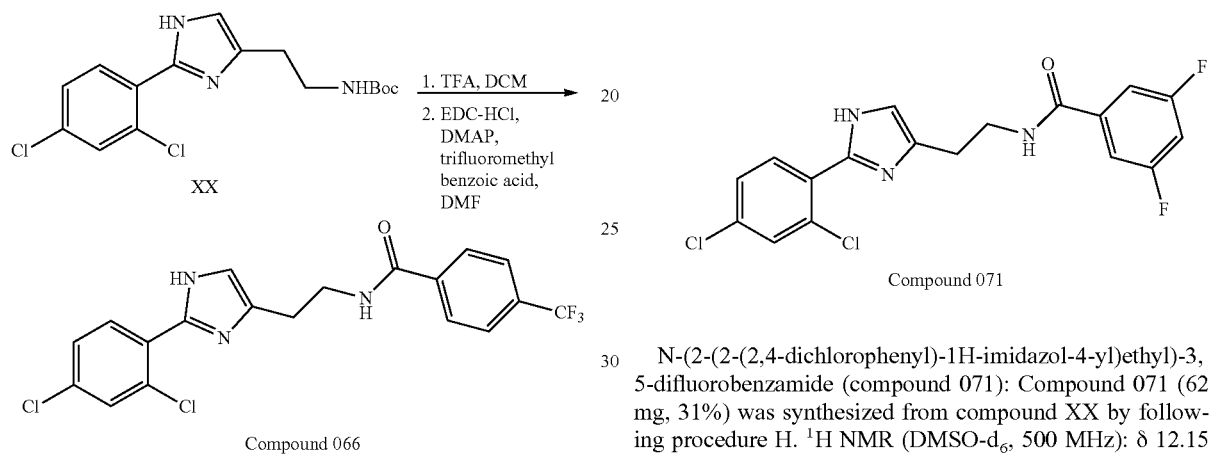

Compound 071

N-(2-(2-(2,4-dichlorophenyl)-1H-imidazol-4-yl)ethyl)-3,5-difluorobenzamide (compound 071): Compound 071 (62 mg, 31%) was synthesized from compound XX by following procedure H. ¹H NMR (DMSO-d$_6$, 500 MHz): δ 12.15 (s, 1H), 8.78 (t, J=5.2 Hz, 1H), 7.81 (s, 1H), 7.71 (d, J=2.1 Hz, 1H), 7.55 (m, 2H), 7.48 (m, 2H), 7.08 (s, 1H), 3.55 (q, J=6.7 Hz, 2H), 2.86 (d, J=28.9 Hz, 2H), 1.23 (s, 1H).

Scheme V

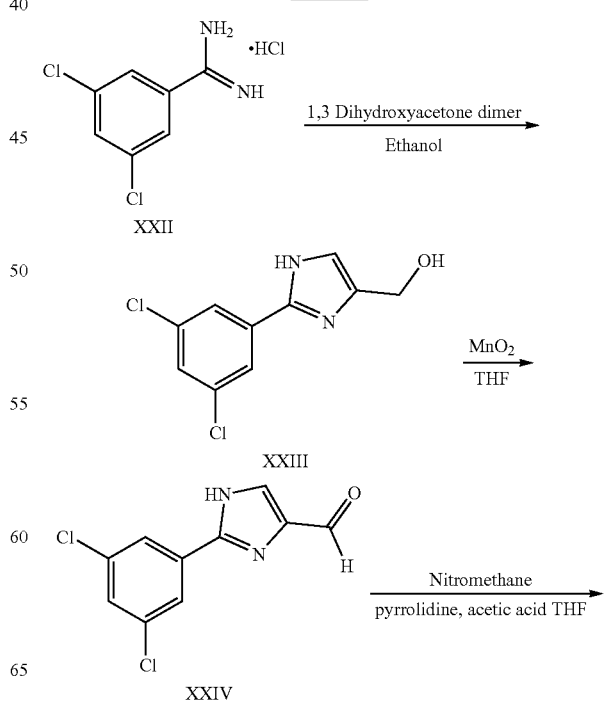

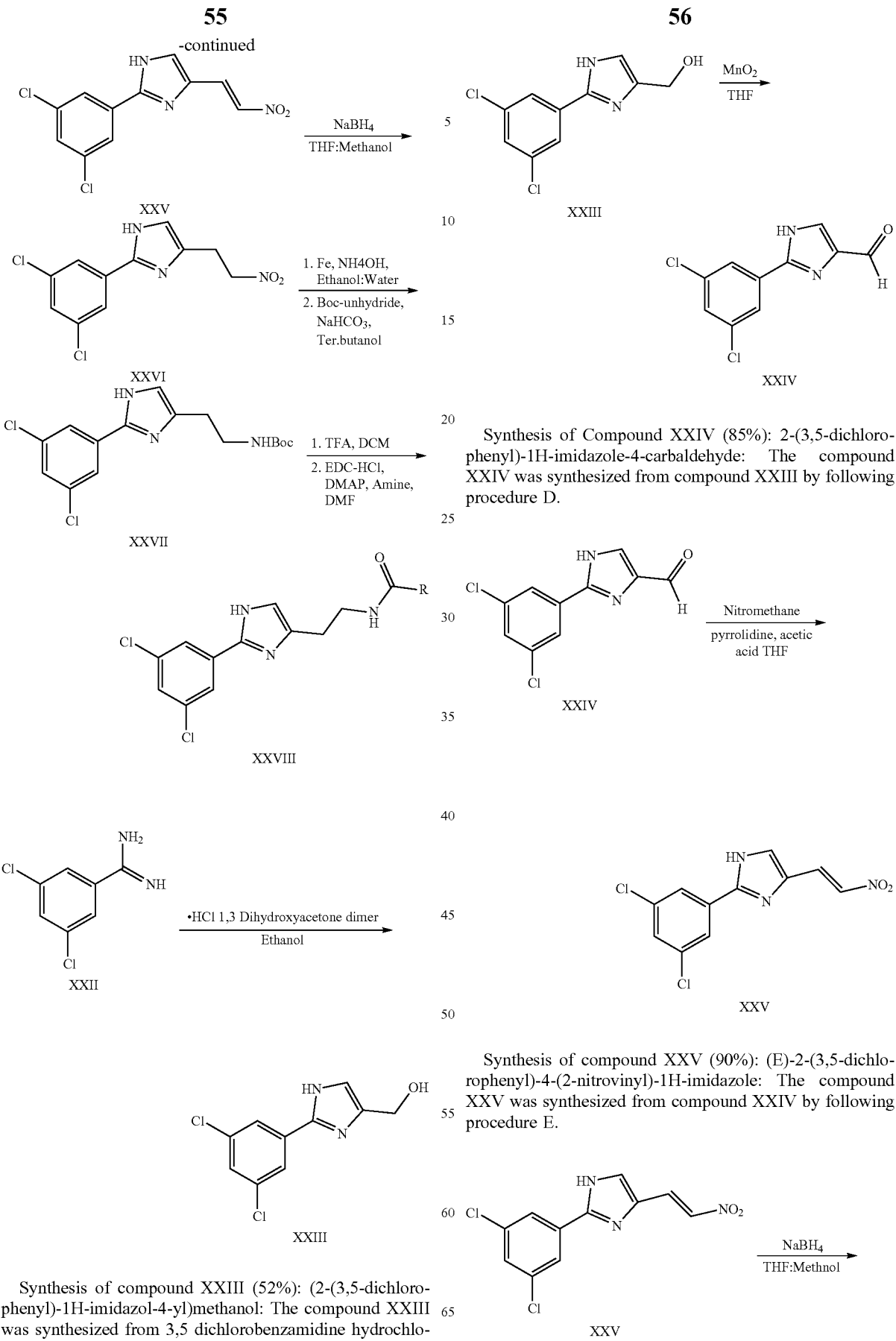

Synthesis of Compound XXIV (85%): 2-(3,5-dichlorophenyl)-1H-imidazole-4-carbaldehyde: The compound XXIV was synthesized from compound XXIII by following procedure D.

Synthesis of compound XXV (90%): (E)-2-(3,5-dichlorophenyl)-4-(2-nitrovinyl)-1H-imidazole: The compound XXV was synthesized from compound XXIV by following procedure E.

Synthesis of compound XXIII (52%): (2-(3,5-dichlorophenyl)-1H-imidazol-4-yl)methanol: The compound XXIII was synthesized from 3,5 dichlorobenzamidine hydrochloride by following procedure A.

-continued

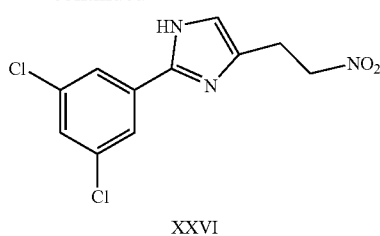

XXVI

Synthesis of compound XXVI (35%): 2-(3,5-dichlorophenyl)-4-(2-nitroethyl)-1H-imidazole: The compound XXVI was synthesized from compound XXV by following procedure F.

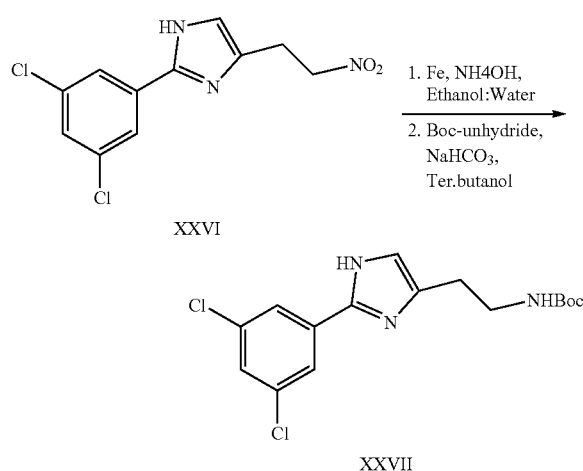

XXVI

XXVII

Synthesis of compound XXVII (45%): tert-butyl (2-(2-(3,5-dichlorophenyl)-1H-imidazol-4-yl)ethyl)carbamate: The compound XXVII was synthesized from compound XXVI by following procedure G.

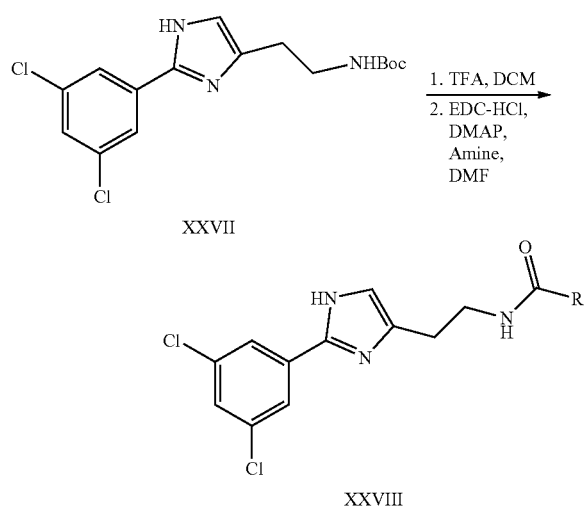

XXVII

XXVIII

Synthesis of general compound XXVIII: The compound XXVIII was synthesized from compound XXVII by following procedure H.

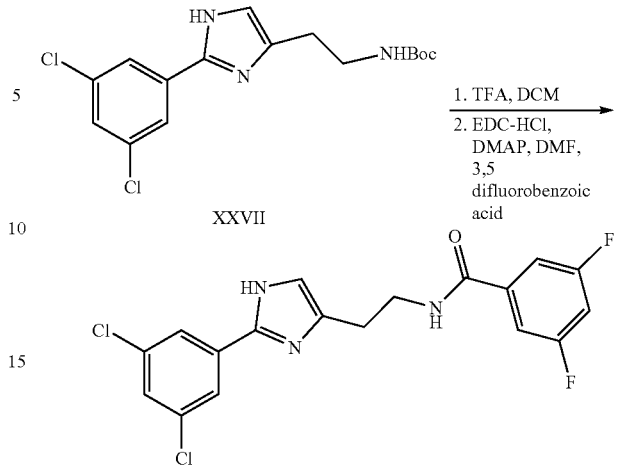

XXVII

Compound 069

N-(2-(2-(3,5-dichlorophenyl)-1H-imidazol-4-yl)ethyl)-3,5-difluorobenzamide (Compound 069): Compound 069 (57 mg, 34%) was synthesized from compound XXVII by following procedure H. $^1$H NMR (DMSO-$d_6$, 500 MHz): δ 12.56 (d, J=15.8 Hz, 1H), 8.75 (m, 1H), 7.91 (d, J=2.1 Hz, 2H), 7.54 (dd, J=12.1 Hz, 7.2 Hz, 3H), 7.46 (m, 1H), 7.14 (s, 1H), 3.53 (q, J=6.7 Hz, 2H), 2.87 (t, J=6.9 Hz, 1H), 2.76 (m, 1H).

Further to the general schemes of preparation as described herein, the present invention envisages all such reaction mechanisms and general reaction schemes that are known from conventional arts and literature resulting in the preparation of the presently claimed compounds.

Experimental Data

Biological Activity of the synthesized compounds

Compounds synthesized under present invention were tested for their in vitro potency. The potency was tested as their ability to protect melanocytes from ER stress induced cell death. ER stress was caused by the treatment of tunicamycin. The results obtained are summarized in Table-I, Table-II and Table-III for mouse B16F10 cells, human A375 cells and human primary melanocytes respectively. Table-IV and Table-V describes the potency of the compounds in effective concentration 50 ($EC_{50}$) which means the dose of compound needed to get the 50% of maximum effect.

The data mentioned below conclusively establish that these compounds improve cell viability under the condition of ER stress. Since ER stress is a causative factor for the commencement of autoimmunity, we envision that these compounds will be effective for the management of the autoimmune indications. These compounds are non-cytotoxic and prevent cells from stress induced damages, a condition seen in vitiligo and other autoimmune diseases.

Melanocytes are under tremendous cellular stress in vitiligo patients and are gradually lost whereas their survival and escape from cellular stress is achieved by these imidazole compounds. Hence, these compounds can be used to treat autoimmune vitiligo.

Furthermore, increased cellular stress is a mechanism for the initiation of the autoimmunity, the compounds of present invention can be utilized for treatment and/or prevention of autoimmune diseases such as skin autoimmune diseases including vitiligo, psoriasis, atopic dermatitis, alopecia areata, SLE, Bullous, pemphigus, scleroderma; and other autoimmune diseases including rheumatoid arthritis, type-I diabetes, celiac disease, inflammatory bowel diseases, Crohn's disease etc. The present invention clearly establishes the unexpected utility of these imidazole compounds to treat and prevent these diseases.

TABLE I

List of Compounds and their potency (at 25-30 μM concentration) in mouse B16F10 cells

|    | Compound No. | % Recovery |
|----|--------------|------------|
| 1  | 001          | 52         |
| 2  | 002          | 58         |
| 3  | 003          | 17         |
| 4  | 004          | 22         |
| 5  | 005          | 38         |
| 6  | 006          | 31         |
| 7  | 007          | 38         |
| 8  | 008          | 39         |
| 9  | 009          | 36         |
| 10 | 010          | 12         |
| 11 | 011          | 18         |
| 12 | 012          | 15         |
| 13 | 013          | 40         |
| 14 | 014          | 52         |
| 15 | 016          | 14         |
| 16 | 017          | 29         |
| 17 | 019          | 36         |
| 18 | 020          | 17         |
| 19 | 022          | 44         |
| 20 | 025          | 55         |
| 21 | 026          | 15         |
| 22 | 051          | 22         |
| 23 | 050          | 35         |
| 24 | 046          | 27         |
| 25 | 055          | 10         |
| 26 | 053          | 24         |
| 27 | 054          | 33         |
| 28 | 066          | 50         |
| 29 | 067          | 40         |
| 30 | 068          | 21         |
| 31 | 070          | 51         |
| 32 | 071          | 58         |

TABLE II

List of Compounds and their potency (at 25-30 μM concentration) in human A375 cells

|    | Compound No. | % Recovery |
|----|--------------|------------|
| 1  | 001          | 25         |
| 2  | 002          | 22         |
| 3  | 003          | 13         |
| 4  | 004          | 32         |
| 5  | 007          | 19         |
| 6  | 010          | 17         |
| 7  | 014          | 36         |
| 8  | 016          | 17         |
| 9  | 022          | 18         |
| 10 | 025          | 57         |
| 11 | 026          | 50         |
| 12 | 027          | 56         |
| 13 | 051          | 50         |
| 14 | 050          | 27         |
| 15 | 046          | 63         |
| 16 | 055          | 59         |
| 17 | 064          | 65         |
| 18 | 053          | 65         |
| 19 | 054          | 58         |
| 20 | 066          | 44         |
| 21 | 067          | 54         |
| 22 | 068          | 42         |
| 23 | 069          | 88         |
| 24 | 070          | 44         |
| 25 | 071          | 39         |

TABLE III

List of Compounds and their potency (at 25-30 μM concentration) in human primary melanocytes (NHEM: Normal Human Epidermal Melanocytes)

|    | Compound No. | % Recovery |
|----|--------------|------------|
| 1  | 002          | 17         |
| 2  | 025          | 41         |
| 3  | 026          | 30         |
| 4  | 027          | 33         |
| 5  | 051          | 35         |
| 6  | 050          | 5          |
| 7  | 046          | 10         |
| 8  | 055          | 13         |
| 9  | 064          | 38         |
| 10 | 053          | 37         |
| 11 | 054          | 46         |

TABLE IV

EC50 (μM) of NCEs in mouse B16F10 cells

|    | Compound No. | EC50 (μM) |
|----|--------------|-----------|
| 1  | 002          | 2.71      |
| 2  | 021          | 55.7      |
| 3  | 022          | 13.7      |
| 4  | 025          | 3.3       |
| 5  | 026          | 8.6       |
| 6  | 053          | 18.1      |
| 7  | 066          | 7.2       |
| 8  | 067          | 9.7       |
| 9  | 068          | 33.8      |
| 10 | 070          | 11.9      |
| 11 | 071          | 10.9      |

TABLE V

EC50 (μM) of NCEs in Human A375 cells

|    | Compound No. | EC50 (μM) |
|----|--------------|-----------|
| 1  | 002          | 20.6      |
| 2  | 014          | 33.3      |
| 3  | 025          | 14.2      |
| 4  | 026          | 18.6      |
| 5  | 027          | 14.9      |
| 6  | 051          | 5.9       |
| 7  | 050          | 33.4      |
| 8  | 046          | 7.9       |
| 9  | 055          | 8.9       |
| 10 | 064          | 4.9       |
| 11 | 053          | 2.9       |
| 12 | 054          | 2.9       |
| 13 | 066          | 12.1      |
| 14 | 067          | 3.1       |
| 15 | 068          | 9         |
| 16 | 069          | 1.2       |
| 17 | 070          | 8.1       |
| 18 | 071          | 10.5      |

For the estimation of potency, mouse B16F10, human A375 or human primary melanocytes (NHEM) cells were pretreated in quadruplicates with these compounds for 6 hours. After 6 hours of incubation, tunicamycin was added at either 300 ng/ml for B16F10 cells or at 100 ng/ml for A375 cells or at 200 ng/ml for NHEM to induce stress mediated cell death and cultured further for a total of 72 hours. The vehicle (DMSO) concentration was kept constant for each well. After 72 hours of treatment, MTT assay was performed to measure the cell growth and vehicle control was kept at 100%. Effect of the treatment of compounds was calculated as cell growth over tunicamycin treatment. For the estimation of Effective Concentration 50 ($EC_{50}$), cells were treated with different concentration of compounds along with tunicamycin and MTT assay was performed. The $EC_{50}$ values were calculated by GraphPad Prism 7 software.

The invention claimed is:

1. A pharmaceutical compound of formula I:

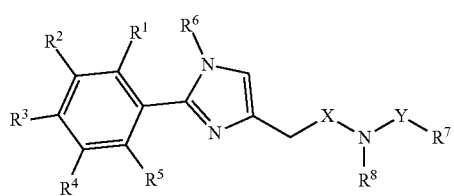

Formula - I wherein, $R^1$, $R^2$, $R^3$, $R^4$, $R^5$ are each independently selected from a hydrogen, halogen, straight chain or branched alkyl, straight chain or branched alkenyl, straight chain or branched alkoxyalkyl, phenyl, aryl, aralkyl, alkoxy alkyl, alkoxy aryl, aromatic or aliphatic heterocycle comprising at least one hetero atom selected from a group of O, N and S, with the proviso that $R^1$, $R^2$, $R^3$, $R^4$ and $R^5$ are not hydrogen at the same time;

any of two adjacent R groups form a 5-6 membered aromatic or aliphatic ring comprising at least one hetero atom selected from a group of O, N and S;

$R^6$ independently selected from hydrogen, straight chain or branched C1-C5 alkyl;

X is selected from $CH_2$ or C=O, wherein when X is $CH_2$, Y is C=O, and when X is C=O, Y is absent;

$R^7$ and $R^8$ are each independently selected from hydrogen, straight chain or branched alkyl, straight chain or branched aralkyl, straight chain or branched alkenyl, straight chain or branched alkynyl, characterized in that together they form a 3-7 membered aromatic or aliphatic heterocycle comprising at least one hetero atom selected from O, N, and S, —$CH_2$ ($CH_2$)$_n$$NR_cR_d$ wherein n is 0-3, and $R_c$ and $R_d$ are both independently selected from alkyl or together form a 3-7 membered aromatic or aliphatic heterocycle comprising at least one hetero atom selected from a group of O, N and S; including stereoisomers, pure or mixed, racemic mixtures, geometrical isomers, tautomers, pharmaceutically acceptable salts, hydrates, solvates, solid forms and mixtures thereof.

2. The pharmaceutical compound of claim 1, wherein R1, R2, R3, R4, R5, R6, R7, R8 may be substituted or remain unsubstituted.

3. The pharmaceutical compound of claim 1 selected from the group consisting of:

2-(2-(4-chlorophenyl)-1H-imidazol-4-yl)-N-(4-fluorophenethyl) acetamide;

N-(2-(2-(4-chlorophenyl)-1H-imidazol-4-yl) ethyl) butyramide;

2-(2-(4-chlorophenyl)-1H-imidazol-4-yl)-N-(2-morpholinoethyl) acetamide;

N-butyl-2-(2-(4-chlorophenyl)-1H-imidazol-4-yl) acetamide;

N-butyl-2-(2-(4-chlorophenyl)-1-methyl-1H-imidazol-4-yl) acetamide;

2-(2-(4-chlorophenyl)-1-methyl-1H-imidazol-4-yl)-N-(2-morpholinoethyl) acetamide;

2-(2-(4-chlorophenyl)-1-methyl-1H-imidazol-4-yl)-N-(3-(trifluoromethyl) phenyl) acetamide;

2-(2-(4-chlorophenyl)-1-methyl-1H-imidazol-4-yl)-N-(3-isopropoxypropyl) acetamide;

2-(2-(4-chlorophenyl)-1H-imidazol-4-yl)-N-(3-(trifluoromethyl) phenyl) acetamide;

2-(2-(4-chlorophenyl)-1H-imidazol-4-yl)-N-(3-isopropoxypropyl) acetamide;

2-(2-(4-chlorophenyl)-1H-imidazol-4-yl)-N-(4-fluorophenyl) acetamide;

2-(2-(4-chlorophenyl)-1H-imidazol-4-yl)-1-(4,4-difluoropiperidin-1-yl) ethan-1-one;

2-(2-(4-chlorophenyl)-1-methyl-1H-imidazol-4-yl)-N-(4-fluorophenyl) acetamide;

2-(2-(4-chlorophenyl)-1H-imidazol-4-yl)-N-(4-(trifluoromethyl) phenyl) acetamide;

2-(2~ (4-chlorophenyl)-1-methyl-1H-imidazol-4-yl)-N-(4-(trifluoromethyl) phenyl) acetamide;

2-(2-(4-chlorophenyl)-1H-imidazol-4-yl)-1-(pyrrolidin-1-yl) ethan-1-one;

2-(2-(4-chlorophenyl)-1-methyl-1H-imidazol-4-yl)-1-(pyrrolidin-1-yl) ethan-1-one;

2-(2-(4-chlorophenyl)-1-methyl-1H-imidazol-4-yl)-N-cyclopentylacetamide;

2-(2-(4-chlorophenyl)-1H-imidazol-4-yl)-N-cyclopentylacetamide;

2-(2-(4-chlorophenyl)-1H-imidazol-4-yl)-1-(4-methylpiperazin-1-yl) ethan-1-one;

2-(2-(4-chlorophenyl)-1-methyl-1H-imidazol-4-yl)-1-(4-methylpiperazin-1-yl) ethan-1-one;

2-(2-(4-chlorophenyl)-1-methyl-1H-imidazol-4-yl)-N-(4-fluorophenethyl) acetamide;

2-(2-(4-chlorophenyl)-1H-imidazol-4-yl)-1-morpholinoethan-1-one;

2-(2-(4-chlorophenyl)-1H-imidazol-4-yl)-1-thiomorpholinoethan-1-one;

N-(2-(2-(4-chlorophenyl)-1H-imidazol-4-yl) ethyl)-3,3-dimethylbutanamide;

N-(2-(2-(4-chlorophenyl)-1H-imidazol-4-yl) ethyl)-2,2-dimethylbutanamide;

N-(2-(2-(4-chlorophenyl)-1H-imidazol-4-yl) ethyl)-3-methylbutanamide;

N-(2-(2-phenyl-1H-imidazol-4-yl) ethyl) butyramide;

N-(2-(2-(3-(1H-pyrazol-1-yl) phenyl)-1H-imidazol-4-yl) ethyl) butyramide;

N-(2-(2-(4-methoxyphenyl)-1H-imidazol-4-yl) ethyl) butyramide;

N-(2-(2-(4-phenoxyphenyl)-1H-imidazol-4-yl) ethyl) butyramide;

N-(2-(2-(pyridin-4-yl)-1H-imidazol-4-yl) ethyl) butyramide;

N-(2-(1-methyl-2-(pyridin-4-yl)-1H-imidazol-4-yl) ethyl) butyramide;

N-(2-(2-(3-(1H-pyrrol-2-yl) phenyl)-1H-imidazol-4-yl) ethyl) butyramide;
N-(2-(2-(p-tolyl)-1H-imidazol-4-yl) ethyl) butyramide;
N-(2-(2-(3,5-dichlorophenyl)-1H-imidazol-4-yl) ethyl) butyramide;
N-(2-(2-([1,1'-biphenyl]-3-yl)-1H-imidazol-4-yl) ethyl) butyramide;
N-(2-(2-(4-vinylphenyl)-1H-imidazol-4-yl) ethyl) butyramide;
N-(2-(2-(3-(1H-pyrrol-2-yl) phenyl)-1-methyl-1H-imidazol-4-yl) ethyl) butyramide;
N-(2-(2-(3-morpholinophenyl)-1H-imidazol-4-yl) ethyl) butyramide;
N-(2-(2-(3-(piperidin-1-yl) phenyl)-1H-imidazol-4-yl) ethyl) butyramide;
N-(2-(2-(3-(pyrimidin-5-yl) phenyl)-1H-imidazol-4-yl) ethyl) butyramide;
N-(2-(2-(4-fluorophenyl)-1H-imidazol-4-yl) ethyl) butyramide;
N-(2-(2-(4-benzylphenyl)-1H-imidazol-4-yl) ethyl) butyramide;
N-(2-(1-methyl-2-(3-morpholinophenyl)-1H-imidazol-4-yl) ethyl) butyramide;
N-(2-(2-(4-chlorophenyl)-1H-imidazol-4-yl) ethyl) cyclopropanecarboxamide;
N-(2-(2-(4-chlorophenyl)-1H-imidazol-4-yl) ethyl)-4,4,4-trifluorobutanamide;
N-(2-(2-(4-chlorophenyl)-1H-imidazol-4-yl) ethyl) acetamide;
N-(2-(2-(4-chlorophenyl)-1H-imidazol-4-yl) ethyl)-2-methoxyacetamide;
N-(2~ (2-(4-chlorophenyl)-1H-imidazol-4-yl) ethyl) cyclobutanecarboxamide;
N-(2-(2-(4-chlorophenyl)-1H-imidazol-4-yl) ethyl)-4-fluorobenzamide;
2-((1,S,4R)-bicyclo [2.2.1] heptan-2-yl-N-(2-(4-chlorophenyl)-1H-imidaazol-4-yl) acetamide;
N-(2-(2-(4-chlorophenyl)-1H-imidazol-4-yl) ethyl)-4-(trifluoromethyl) benzamide;
N~ (2-(4-chlorophenyl)-1H-imidazol-4-yl) ethyl)-3,5-difluorobenzamide;
N-(2-(2-(4-chlorophenyl)-1H-imidazol-4-yl) ethyl) cyclopent-1-ene-1-carboxamide;
N-(2-(2-(2,3-dihydrobenzo [b] [1,4]dioxin-6-yl)-1H-imidazol-4-yl) ethyl) cyclopent-1-ene-1-carboxamide;
N-(2-(2-(benzo [d][1,3]dioxol-5-yl)-1H-imidazol-4-yl) ethyl) cyclopent-1-ene-1-carboxamide;
(3r,5r,7r)-N-(2-(2-(4-chlorophenyl)-1H-imidazol-4-yl) ethyl) adamantane-1-carboxamide;
N-(2-(2-(4-chlorophenyl)-1H-imidazol-4-yl) ethyl)-4-methyl-2-(pyridin-2-yl) thiazole-5-carboxamide;
N-(2-(2-(2,4-dichlorophenyl)-1H-imidazol-4-yl) ethyl)-4-(trifluoromethyl) benzamide;
N-(2-(2-(4-chlorophenyl)-1H-imidazol-4-yl) ethyl) hexanamide;
N-(2-(2-(4-chlorophenyl)-1H-imidazol-4-yl) ethyl) octanamide;
N-(2-(2-(3,5-dichlorophenyl)-1H-imidazol-4-yl) ethyl)-3,5-difluorobenzamide;
N-(2-(2-(2,4-dichlorophenyl)-1H-imidazol-4-yl) ethyl)-4-fluorobenzamide;
N-(2-(2-(2,4-dichlorophenyl)-1H-imidazol-4-yl) ethyl)-3,5-difluorobenzamide;
N-(2-(2-(4-chlorophenyl)-1H-imidazol-4-yl) ethyl)-2-(4-(trifluoromethyl) phenyl) acetamide;
N-(2-(2-(4-chlorophenyl)-1H-imidazol-4-yl) ethyl)-3-(4 (trifluoromethyl) phenyl) propenamide;
N-(2-(2-(4-chlorophenyl)-1H-imidazol-4-yl) ethyl)-2-(4-fluorophenyl) acetamide;
N-(2-(2-(4-chlorophenyl)-1H-imidazol-4-yl) ethyl)-3-(4-fluorophenyl) propenamide;
N-(2-(2-(4-chlorophenyl)-1H-imidazol-4-yl) ethyl)-2-(3,5-difluorophenyl) acetamide; and
N-(2-(2-(4-chlorophenyl)-1H-imidazol-4-yl) ethyl)-3-(3,5-difluorophenyl) propenamide.

4. A process to produce the compound of claim 1, with steps comprising of:

a. Reacting chlorobenzamidine hydrochloride in the presence of 1,3 dihydroxyacetone dimer resulting in an imidazole compound of formula II

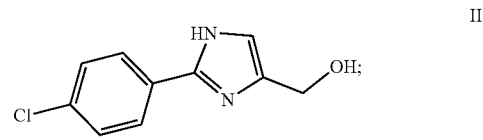 [SMILES: OCc1c[nH]c(-c2ccc(Cl)cc2)n1]

b. Reacting the imidazole moiety formed in step (a) in presence of suitable reagent for chlorination to obtain a compound of formula III

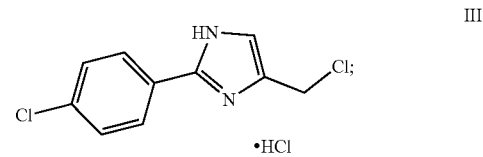 [SMILES: ClCc1c[nH]c(-c2ccc(Cl)cc2)n1 ; Cl]

and then cyanation to obtain a compound of formula IV

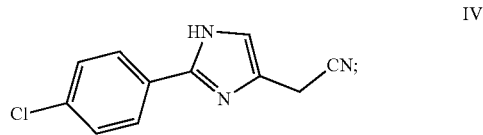 [SMILES: N#CCc1c[nH]c(-c2ccc(Cl)cc2)n1]

in the presence of suitable reagents;

c. Reacting the compound of formula IV to undergo hydrolysis resulting in an imidazole moiety comprising carboxylic acid of formula V

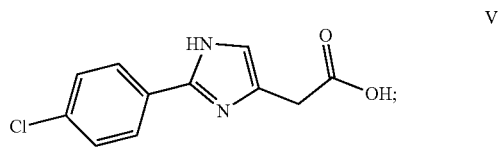 [SMILES: O=C(O)Cc1c[nH]c(-c2ccc(Cl)cc2)n1]

d. Reacting the compound of formula V with the desired reagent and undergoes amide coupling to produce the compounds of formula (I);

Optionally;

e. Reacting the compound of formula IV formed in step (b) with suitable reagents to form a compound of formula VII

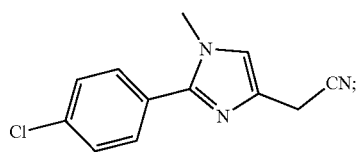

VII f. Reacting the compound of formula VII with the desired reagent and undergoes amide coupling to produce the compound of formula (I).

5. A process to obtain the compound of claim 1, with steps comprising of, a. Reacting chlorobenzamidine hydrochloride or dichlorobenzamidine hydrochloride in the presence of 1,3 dihydroxyacetone dimer resulting in an imidazole compound of formula II

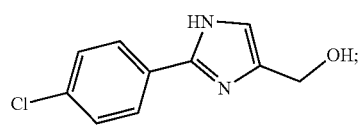

II or XVI

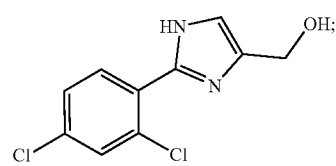

XVI b. Reacting the imidazole compound of formula II or XVI with suitable reagents to obtain a compound of formula X

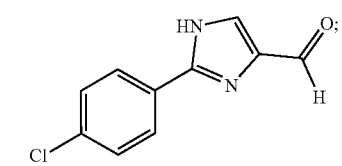

X or
XVII

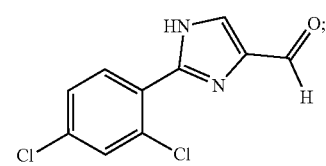

XVII c. Introducing a nitro group to the imidazole compound of formula X or XVII to obtain a compound of formula XI

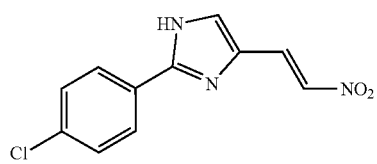

XI or
XVIII

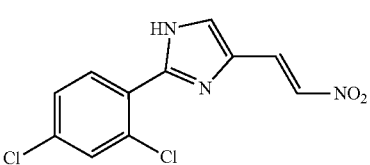

XVIII in the presence of suitable reagents;

d. Hydrogenating the compound of formula XI or XVIII in the presence of suitable reagents to obtain a compound of formula XII

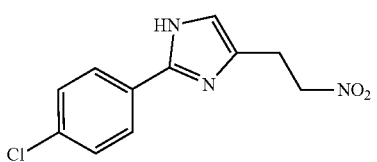

XII or
XIX

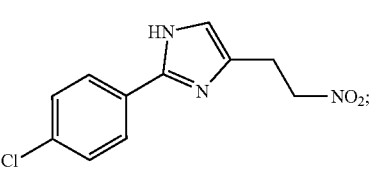

XIX e. Amination of the compound of formula XII or XIX by addition Fe, NH$_4$OH and then Di-tert-butyl dicarbonate to obtain a compound of formula XIII

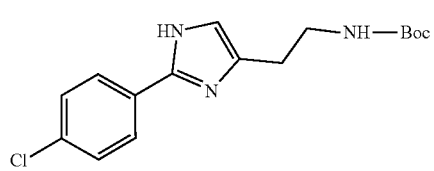

XIII or
XX

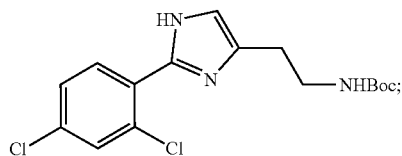 XX f. Treating the compound of formula XIII or XX with desired reagents through amide coupling to obtain the compound of formula I.

6. A pharmaceutical composition comprising an effective amount of the compounds of claim 1 including stereoisomers, pure or mixed, racemic mixtures, geometrical isomers, tautomers, pharmaceutically acceptable salts, hydrates, solvates, solid forms and mixtures thereof, as an active ingredient along with a pharmaceutically acceptable carrier.

7. The process of preparing a pharmaceutical composition of claim 6, comprising the step of mixing the compound of claim 1, with a pharmaceutically acceptable carrier.

8. A method of treating diseases and disorders involving stress mediated cell death, comprising administering a therapeutically effective amount of the compounds of claim 1 including stereoisomers, pure or mixed, racemic mixtures, geometrical isomers, tautomers, pharmaceutically acceptable salts, hydrates, solvates, solid forms and mixtures thereof.

9. The method of claim 8, wherein the disease or disorder is an autoimmune disease or a skin disease.

10. The method of claim 9, wherein the autoimmune disease is a skin autoimmune disease.

11. The method of claim 10, wherein the skin autoimmune disease is selected from the group consisting of psoriasis, lupus, vitiligo, scleroderma, dermatomyositis, epidermolysis bullosa, bullous pemphigoid, leukoderma, dermatitis, and Koebner's phenomenon.

12. The method of claim 8, wherein the mode of administration is selected from a group consisting of oral, parenteral, rectal, topical, intranasal, intravenous, transdermal, sublingual, intramuscular, subcutaneous, and ocular.

13. The pharmaceutical composition of claim 6, wherein the composition is in the form of a formulation that is administered in unit dosage forms selected from tablets, capsules, pills, powders, granules, sterile parenteral solutions or suspensions and oral solutions or suspensions, injections, syrups, liquids, microemulsions, topical creams, ointments, suppositories, sachets, troches and lozenges and oil-water emulsions containing suitable quantities of the compounds of formula I or multiple dosage forms.

* * * * *